US009644006B2

(12) United States Patent
Alonso Martí et al.

(10) Patent No.: US 9,644,006 B2
(45) Date of Patent: May 9, 2017

(54) CARRIER PEPTIDES FOR CELL DELIVERY

(75) Inventors: M. Covadonga Alonso Martí, Madrid (ES); José Ángel Martínez Escribano, Madrid (ES)

(73) Assignee: INSTITUTO NACIONAL DE INVESTIGACIÓN Y TECNOLOGÍA AGRARIA Y ALIMENTARIA (INIA), Madrid (ES)

( * ) Notice: Subject to any disclaimer, the term of this patent is extended or adjusted under 35 U.S.C. 154(b) by 162 days.

(21) Appl. No.: 13/985,747

(22) PCT Filed: Feb. 17, 2012

(86) PCT No.: PCT/EP2012/052773
§ 371 (c)(1),
(2), (4) Date: Oct. 29, 2013

(87) PCT Pub. No.: WO2012/110636
PCT Pub. Date: Aug. 23, 2012

(65) Prior Publication Data
US 2014/0065175 A1    Mar. 6, 2014

(30) Foreign Application Priority Data
Feb. 18, 2011    (EP) .................................... 11155088

(51) Int. Cl.
| | |
|---|---|
| C07K 7/08 | (2006.01) |
| A61K 47/48 | (2006.01) |
| C07K 14/00 | (2006.01) |
| C07K 7/06 | (2006.01) |

(52) U.S. Cl.
CPC ........ *C07K 14/001* (2013.01); *A61K 47/4833* (2013.01); *A61K 47/48246* (2013.01); *A61K 47/48861* (2013.01); *C07K 7/06* (2013.01); *C07K 7/08* (2013.01); *C07K 2319/10* (2013.01); *C07K 2319/70* (2013.01)

(58) Field of Classification Search
None
See application file for complete search history.

(56) References Cited

U.S. PATENT DOCUMENTS 5,312,620 A * 5/1994 Ribi ..................... A61K 9/1273
424/450

FOREIGN PATENT DOCUMENTS

| CA | 2684555 A1 * | 10/2008 |
| WO | 2004015083 A2 | 2/2004 |
| WO | 2009053340 A1 | 4/2009 |

OTHER PUBLICATIONS

Dunn et al., "Dynamics of the unbound head during myosin V processive translocation", Nature Structural & Molecular Biology, 2007, pp. 246-248.*
UniProtKB/Swiss-Prot: Q02440.1, obtained Nov. 3, 2014 from http://www.ncbi.nlm.nih.gov/protein/Q02440.1; pp. 1-8.*
Sugahara et al, "Coadministration of a Tumor-Penetrating Peptide Enhances the Efficacy of Cancer Drugs", Science, 2010, pp. 1031-1035.*
Gupta et al., "Intracellular delivery of large molecules and small particles by cell-penetrating proteins and peptides", Advanced Drug Delivery Reviews, 2005, pp. 637-651.*
Lee et al., "Cell-penetrating chitosan/doxorubicin/TAT conjugates for efficient cancer therapy", International Journal of Cancer, 2011, pp. 2470-2480.*
Zhang et al., "A novel PEGylation of chitosan nanoparticles for gene delivery", Biotechnol. Appl. Biochem., 2007, pp. 197-204.*
Bergen et al., "Evaluation of an LC8-Binding Peptide for the Attachment of Artificial Cargo to Dynein", Molecular Pharmaceutics, 2007, pp. 119-128.*
Alonso et al., "African Swine Fever Virus Protein p54 Interacts with the Microtubular Motor Complex through Direct Binding to Light-Chain Dynein", Journal of Virology, 2001, pp. 9819-9827.*
Mizuno et al., "Identification of the nuclear localization signal of mouse DNA primase: nuclear transport of p46 subunit is facilitated by interaction with p54 subunit", Journal of Cell Science, 1996, pp. 2627-2636.*
Lodish et al., "Chapter 19.3-Kinesin, Dynein, and Intracellular Transport", Molecular Cell Biology. 4th edition., 2000, pp. 1-7.*
Soldati et al., "Powering membrane traffic in endocytosis and recycling", Molecular Cell Biology, 2006, pp. 897-908.*
Lembo et al.,"Nanoparticular delivery systems for antiviral drugs", Antiviral Chemistry and Chemotherapy, 2010, 53-70.*
International Search Report, Sep. 4, 2012.
Bao, L., et al.; "High-titer lentiviral vectors stimulate fetal calf serum-specific human CD4 T-cell responses: implications in human gene therapy," Gene Therapy, 2009, pp. 788-795, vol. 16.
Bareford, Lisa M., et al.; "Endocytic mechanisms for targeted drug delivery," Advanced Drug Delivery Reviews, 2007, pp. 748-758, vol. 59.
Brandén, Lars J., et al.; "A peptide nucleic acid-nuclear localization signal fusion that mediates nuclear transport of DNA," Nature Biotechnology, 1999, pp. 784-787, vol. 17.
Ciolina, Carole, et al.; "Coupling of Nuclear Localization Signals to Plasmid DNA and Specific Interaction of the Conjugates with Importin aplha," Bioconjugate Chem., 1999, pp. 49-55, vol. 10.
Dujardin, Denis L., et al.; "A role for cytoplasmic dynein and LIs1 in directed cell movement," The Journal of Cell Biology, 2003, pp. 1205-1211, vol. 163.
Futaki Shiroh; "Membrane-permeable arginine-rich peptides and the translocation mechanisms," Advanced Drug Delivery Reviews, 2005, pp. 547-558, vol. 57.
Hambley, Trevor W., et al.; "Is Anticancer Drug Development Heading in the Right Direction?" Cancer Res, 2009, pp. 1259-1262, vol. 69.

(Continued)

*Primary Examiner* — Lianko Garyu
(74) *Attorney, Agent, or Firm* — Tristan A. Fuierer; Moore & Van Allen, PLLC

(57) ABSTRACT

The invention relates to the technological sector of the transport and delivery of molecules into cells, either at cytoplasm or at nucleus or inter-cells (cell to cell transport), using peptides binding proteins from the cell microtubule motor complex, preferably dynein-binding peptides, as carrier/delivery peptides; or functionalized structures, as nanoparticles, linked to said carrier/delivery peptides. This delivery can be useful in many technical fields comprising, among some others: diagnosis, therapy and pharmacology.

5 Claims, 14 Drawing Sheets

(56) References Cited

OTHER PUBLICATIONS

Figure 1:
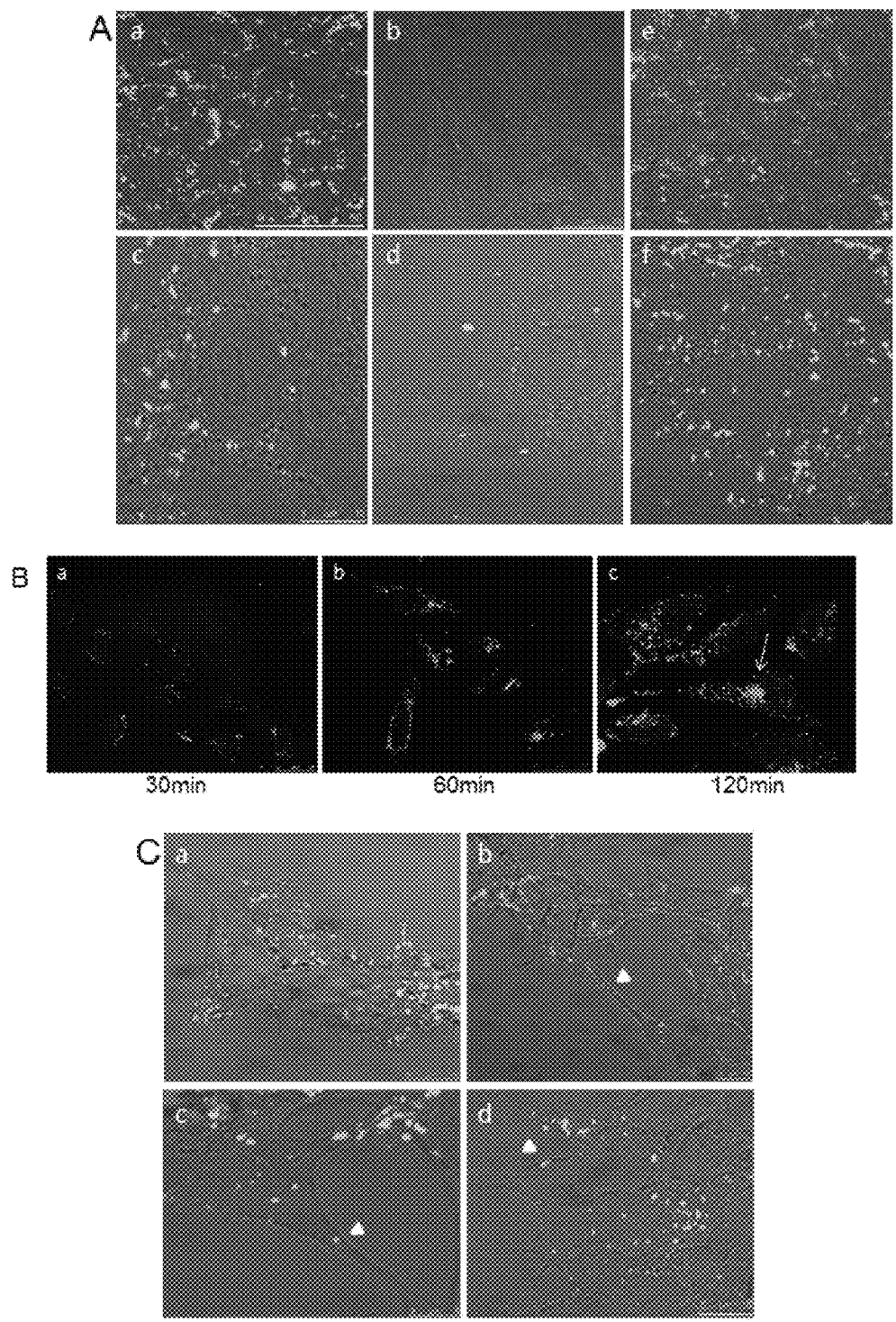

Howard, Melissa D., et al.; "PEGylation of Nanocarrier Drug Delivery Systems: State of the Art," Journal of Biomedical Nanotechnology, 2008, pp. 133-148, vol. 4—Abstract Only.

Ichinohe, Takeshi, et al.; "Influenza virus activates inflammasomes via its intracellular M2 ion channel," Nature Immunology, 2010, pp. 404-410, vol. 11.

Iyer, Arun K., et al.; "Exploiting the enhanced permeability and retention effect for tumor targeting," Drug Discovery Today, 2006, pp. 812-818, vol. 11.

Liao, Chen, et al.; "Over-expression of LTPS-L in hepatocellular carcinoma cell line SMMC-7721 induces crisis," World Journal of Gastroenterology, 2002, pp. 1050-1052, vol. 8.

Melo, Sonia A., et al.; "A Genetic Defect in Exportin-5 Traps Precursor MicroRNAs in the Nucleus of Cancer Cells," Cancer Cell, 2010, pp. 303-315, vol. 18.

Moffatt, Stanley, et al.; "Circumvention of Vector-Specific Neutralizing Antibody Response by Alternating Use of Human and Non-Human Adenoviruses: Implications in Gene Therapy," Virology, 2000, pp. 159-167, vol. 272.

Panté, Nelly, et al.; "Nuclear Pore Complex Is Able to Transport Macromolecules with Diameters of ~39 nm," Molecular Biology of the Cell, 2002, pp. 425-434, vol. 13.

Rodríguez, Javier M., et al.; "African Swine Fever Virus Structural Protein p54 Is Essential for the Recruitment of Envelope Precursors to Assembly Sites," Journal of Virology, 2004, pp. 4299-4313, vol. 78.

Rothbard, Jonathan B., et al.; "Role of Membrane Potential and Hydrogen Bonding in the Mechanism of Translocation of Guanidinium-Rich Peptides into Cells," Journal of American Chemical Society, 2004, pp. 9506-9507, vol. 126.

Salina, Davide, et al.; "Cytoplasmic Dynein as a Facilitator of Nuclear Envelope Breakdown," Cell, 2002, pp. 97-107, vol. 108.

Sandgren, Staffan, et al.; "Nuclear Targeting of Macromolecular Polyanions by an HIV-Tat Derived Peptide," The Journal of Biological Chemistry, 2002, pp. 38877-38883, vol. 277.

Sebestyén, Magdolna G., et al.; "DNA vector chemistry: The covalent attachment of signal peptides to plasmid DNA," Nature Biotechnology, 1998, pp. 80-85, vol. 16.

Subramanian, Ajit, et al.; "Nuclear targeting peptide scaffolds for lipofection of nondividing mammalian cells," Nature Biotechnology, 1999, pp. 873-877, vol. 17.

Sugahara, Kazuki N., et al.; "Tissue-Penetrating Delivery of Compouds and Nanoparticles into Tumors," Cancer Cell, 2009, pp. 510-520, vol. 16.

Templeton, Allen C., et al.; "Water-Soluble, Isolable Gold Clusters Protected by Tiopronin and Coenzyme A Monolayers," Langmuir, 1999, pp. 66-76, vol. 15.

Wadia, Jehangir S., et al.; "Transducible TAT-HA fusogenic peptide enhances escape of TAT-fusion proteins after lipid raft macropinogytosis," Nature Medicine, 2004, pp. 310-315, vol. 10.

Wagner, Ernst; "Application of membrane-active peptides for nonviral gene delivery," Advanced Drug Delivery Reviews, 1999, pp. 279-289, vol. 38.

Wang, Guoxing, et al.; "Nucleophosmin/B23 Inhibits Eg5-mediated Microtubule Deploymerization by Inactivating Its ATPase Activity," The Journal of Biological Chemistry, 2010, pp. 19060-19067, vol. 285.

Zaro, Jennica L., et al.; "Quantitative comparison of membrane transduction and endocytosis of oligopeptides," Biochemical and Biophysical Research Communications, 2003, pp. 241-247, vol. 307.

Zhou, Xiao Zhen., et al.; "The Pin2/TRF1-Interacting Protein PinX1 Is a Potent Telomerase Inhibitor," Cell, 2001, pp. 347-359, vol. 107.

Ziegler, André, et al.; "The Cationic Cell-Penetrating Peptide CPP TAT Derived from the HIV-1 Protein TAT Is Rapidly Transported into Living Fibroblasts: Optical, Biophysical, and Metabolic Evidence," Biochemistry, 2005, pp. 138-148, vol. 44.

\* cited by examiner

CARRIER PEPTIDES FOR CELL DELIVERY

CROSS-REFERENCE TO RELATED APPLICATIONS

This application is filed under the provisions of 35 U.S.C. §371 and claims the priority of International Patent Application No. PCT/ES2012/052773 filed on 17 Feb. 2012 entitled "CARRIER PEPTIDES FOR CELL DELIVERY" in the name of M. Covadonga ALONSO MARTI, et al, which claims priority to European Patent Application No. EP 11155088.5, filed on 18 Feb. 2011, both of which are hereby incorporated by reference herein in their entirety.

FIELD OF THE INVENTION

The invention relates to the technological sector of the delivery of molecules into cells, either at cytoplasm or at nucleus or inter-cells (cell to cell transport). This delivery can be useful in many technical fields comprising, among some others: diagnosis, therapy and pharmacology.

STATE OF THE ART

Many new therapeutic approaches and drugs have been developed in recent years and their therapeutic efficacy has been proved to be highly dependent on the drug delivery system used. The development of peptide carriers which are able to deliver a drug to its intracellular destination, enhancing its accumulation and increasing cell to cell spread, would significantly improve the efficacy and reduce toxicity of any given therapy.

There are several biological barriers at the cellular level that a given drug or payload must overcome. Among them, the cell membrane and the submembranous actin cortical layer, can be mentioned. The following hurdle, once carrier peptides have entered into the cell, it would be to escape lysosomal degradation. The receptor-mediated endocytosis is probably the most common pathway for the specific uptake of macromolecules. The exact mode of endocytosis is important because it determines the path of trafficking through various possible subcellular compartments (Zaro). In most cases, endosomal escape must occur before fusion with a lysosome to prevent degradation by the acidic lysosomal pH. After that, endosomal escape is necessary to allow access of the carrier to other subcellular compartments, the cytosol or the nucleus.

Most of the viruses and toxins have evolved well-defined machinery to infect the cells and to reach the cell nucleus. In fact, there is wide experience in the use of viral vectors in gene therapy but this approach has the undesired side effects of introducing many other viral genes with a variety of functions in the host cell, the risk of virus-mediated mutagenesis, the preexisting immunity against the viral vector or the elicitation of an immune response against the vector itself (Moffat) or to fetal calf serum after repeated injections (Bao).

First barrier: The extracellular membrane; In the context of drug delivery, peptides have been used to overcome the extracellular membrane barrier, so called "cell-penetrating peptides" (CPPs) for the transport of various cargoes with molecular weights several times greater than the molecular weight of the carrier peptide itself (Futaki). Most of them have been designed to overcome one or two cellular barriers but are inefficient against the others. The exact mechanism of internalization of these peptides, which gain direct access to the cell cytoplasm independent of the cell type, is still unclear, but seems to depend on each type of peptide. More than one single mechanism is assumed to be responsible for internalization of various cargo molecules (Zaro, Ziegler). A CPP of viral origin (from Human Immunodeficiency virus Tat protein) called Tat peptide mediated delivery has been proposed to proceed via energy-dependent macropinocytosis with subsequent escape from the endosome to the cytoplasm and eventually its transport into the nucleus through nuclear pores (Wadia). Other CPPs penetrate cells via electrostatic interactions and hydrogen bonding in non-energy dependent mechanisms but their intracellular diffusion capability is much more limited (Rothward).

Second barrier: endosomal membrane. After entering the cell by any mechanism, a second step would be to avoid lysosomal degradation by endocytosis, also known as endosomal escape. Previous described approaches were designed to facilitate endosomal escape (Wagner).

Third barrier: the cytosolic enzymes. Once the delivered compound is free in the cytosol could be quickly degraded. Nucleic acids as DNA and other chemical compounds in the cytoplasm would be susceptible to degradation by nucleases, as DNAses and many other proteolytic enzymes and would not be able to reach, by simple diffusion, the desired cell compartment in a crowded cellular environment.

Fourth barrier: the nuclear membrane in and out. For drugs to reach the nucleus as the site of action (such as hormones, plasmid DNA, DNA intercalators), crossing the nuclear membrane supposes another barrier to drug delivery. Nuclear uptake of plasmid DNA is the rate-limiting step in efficient transfection and successful gene therapy. The nucleus is separated from the cytosol by two membranes which are interrupted by the nuclear pores (Pante). Certain peptide sequences, known as nuclear localization signals (NLS) have been reported to specifically interact with the cytoplasmic factors which can then transport molecules through the nuclear pore. This transport has size limitations estimated for molecules about 40-45 kDa and less than 100 nm of diameter, as average. NLS are peptides with no general consensus sequence, mostly composed of basic amino acids.

Several approaches to mediate enzymes or nucleic acids delivery to the nucleus have been reported for gene therapy or transfection. However, nucleic acids as DNA, in the cytoplasm, are susceptible to degradation by nucleases as DNAses and the mobility of bigger DNA fragments is restricted due to the crowded cytosolic environment. Moreover, entry of the DNA into the nucleus heavily relies on the breakdown of the nuclear envelope that regularly only occurs during mitosis.

As the delivery of the DNA to the nucleus is one of the major bottlenecks in non-viral gene delivery, the coupling of peptides containing a NLS, to plasmid or linear DNA, is the current approach towards increased delivery of these cargo molecules to the nucleus. Various NLS, among other the SV40 large T-antigen derived peptide (Branden, Sebestyen), the NLS from HIV Tat (Sandgren) or the M9 sequence from the heterogeneous nuclear ribonucleoprotein (Subramanian), have been tested. Despite the promising concept, there is a lack of consensus concerning the potency of NLS-peptides in nucleic acid delivery. Some studies have shown the successful nuclear delivery of oligonucleotides or linearized plasmids functionalized by an NLS (Branden), but the transfer of intact plasmids or bigger nucleic acid molecules is less efficient due to limitations of the nuclear pore size (Ciolina). Moreover, recent reports suggested that some tumors present genetic defects in nuclear export machinery with an associated retention of microRNAs inside the nucleus that would severely impair effective production of the delivered gene of interest (Melo).

Targeting of anticancer drugs to tumors poses further difficulties in delivery; drugs only penetrate a few cells around blood vessels (Hambley and Hait, Iyer). This problem is particularly difficult with solid tumors which are poorly perfused and blood vessels and lymphatics are usually dysfunctional. Solid tumors exhibit high interstitial pressure and the leakiness of tumor vessels impairs enhanced permeability and retention effect (Sugahara). Interstitial fibrosis can further retard the diffusion of compounds through tumor.

Results with nanoparticles targeted to tumor cells is also limited using previous approaches. Nanoparticles are small particles (from a few to 200 nm in diameter, as average), that can serve as carriers of drugs or pharmaceutical compounds and contrast agents for imaging in medicine, allowing many different loads and increasing stability and pharmacokinetic properties of drugs to be delivered. Although small in comparison with cells, nanoparticles are much larger than most molecules and are less likely to penetrate membranes and gain access to tumor cells than drugs having smaller molecular mass, peptides or even than antibodies.

Surprisingly, the present invention can overcome all previously listed barriers and limitations. The single inventive concept underlying on present invention and linking all the different invention's embodiments disclosed and/or claimed hereto, it is the unexpected discovery of the use of peptides that can interact with the cellular transport machinery linked to microtubules, for transport and delivery of molecules, without size restriction, inside the cell. This transport and delivery includes carrying molecules in and out the cell nucleus and cell-to-cell transport and delivery, as well. Those peptides mimic the ultimate mechanisms of cellular transport as a whole, without the undesired effects of a viral vector. Moreover, the molecules transported by the peptides of the invention, keep their physical, chemical, biological and functional properties, during the transport and delivery process.

For the purpose of present invention the term "peptides binding proteins from the cell microtubule motor complex" must be interpreted as peptides able to bind to the aforesaid proteins. Analogously, "dynein-binding peptides" must be read as peptides able to bind to dynein.

Microtubule dependent transport is very efficient in transporting proteins, nucleic acids and organelles in the normal cell. The invention is based in said microtubule transport and comprises carrier peptides that engage a molecule of the microtubule motor system and, thus can go across cytosol with payloads ranking from few amino acids, to organelle size, towards the perinuclear area at the microtubule organizing centre (MTOC). The use of this cell molecular motor based transport system has no precedent in the current state of the art of cell transport/delivery. Only viruses in nature have evolved mechanisms to engage any protein of the microtubule motor complex and by this means be transported through the cytoplasm. Furthermore, the most unexpected feature of the present invention is the possibility to manipulate this cellular transport to overcome not just cytosol, but any other existing cellular barrier selected from: nuclear membrane, traffic in-and-out the nucleus, cytoplasm and cytoplasmic membrane. This allows traffic crossing from one cell to another, projecting loads to cell projections and through cell-cell contacts as we will show below, by a quick intra- and inter-cellular transport movement beyond cellular boundaries.

In general, molecular motors are biological molecular machines that are the essential agents of movement in living organisms. Generally speaking, a motor may be defined as a device that consumes energy in one form and converts it into motion or mechanical work; for example, many protein-based molecular motors harness the chemical free energy released by the hydrolysis of ATP in order to perform mechanical work. Some examples of molecular motors are actin, dynein, kinesin, myosin, calmodulin, dynamin, ATP synthase, helicases, polymerases, topoisomerases, prestin, etc.

Motor proteins are a class of molecular motors that are able to move along the surface of a suitable substrate. They are powered by the hydrolysis of ATP and convert chemical energy into mechanical work. Some of these cellular motor proteins are associated to the cytoskeleton and move along microtubule filaments. In the normal cell, cytoskeleton motor proteins are organized in the microtubule motor complex system.

Microtubule motor complex system is a large macromolecular complex composed by different motor proteins such as dynein, dynactin, p150-Glued and regulatory proteins such as LIS1 NDEL1, NDE1 and NUDC. Motor proteins are the driving force behind most active transport of proteins and vesicles in the cytoplasm. Kinesins and dyneins play essential roles in intracellular transport such as axonal transport and in the formation of the spindle apparatus and the separation of the chromosomes during mitosis and meiosis.

Dynein is a protein from the microtubule motor complex, which is composed by heavy, intermediate and light chains. Several families of dynein light chains have been described. There are up to six light chains belonging to three protein families (DYNLL/DLC8, DYNLT/tctex, and DYNLRB/LC7/roadblock), two light intermediate chains (DYNC1LI or DLIC), and two intermediate chains (DYNC1I or DIC), all of which have been implicated in cargo binding and they are able to transport a wide range of loads. Heavy chains are globular proteins that produce adenosine triphosphate (ATP) hydrolysis in order to generate the energy necessary for movement. In fact, dynein is responsible of repositioning of Golgi apparatus after cell mitosis, giving an idea of the capability of this molecule to transport big sized organelles. Kinesins are involved in reposition of dynein to the microtubule tips at the cell periphery, called plus-ends, where it accumulates. Plus-ends are the microtubule growing ends. There are other functions of dynein at the microtubule plus-ends such as cortical capture of microtubules, delivery of signals that regulate actin cytoskeleton and capture of vesicular cargo for dynein dependent movement. Molecular motor dynein and associated molecules (dynactin, p150$^{glued}$ etc.) are part of a multifunctional motor complex involved in cell polarization, lamellipodia and filopodia emissions, which increase cell to cell contacts (Dujardin).

The peptide carrier moieties capable to bind microtubule motor dynein that are object of the present invention, would allow the delivery of molecules or structures (cargoes) not only within the cell, but also in-and-out the cell nucleus, from one cell to another, hence quickly spreading to neighboring cells. The carrier peptides of present invention are able to take advantage of microtubule motor complex properties and master the permeability of the nucleus compartment by themselves as it is demonstrated in the present invention, due to the unique property of dynein to disassemble nuclear envelope (Salina) beyond the intrinsic size limitations of the nuclear pore transport of NLSs. Although dynein has been used as proof of concept for present invention, the technical solution offered by the aforesaid invention, as disclosed hereto, is not limited to peptides binding dynein but to any peptide binding proteins from cell microtubule complex. As matter of fact, in Table 1, apart from the peptides binding dynein comprising the amino acid sequences represented by SEQ ID NO: 1 to 10, and the comparative control represented by SEQ ID NO: 12, a further peptide from molecular motor myosin, is also mentioned (TransMy, represented by SEQ ID NO: 11).

In this invention, it is shown the unexpected dynamic properties of peptides sharing as technical feature their binding capacity to a natural cellular molecular motor protein, one of the components of the microtubule motor complex, preferably cellular dynein. The present invention focuses on the use of those peptides for carrier and/or delivery purposes, powered by the cellular motor complex. Those peptides allow rapid movement of loaded substances inside the cell, across the cytoplasm, in-and-out the cell nucleus and from cell to cell, being the first consequence that this transport boosts cellular uptake efficiency of the desired substances to be delivered.

Also, this invention shows that those peptides are useful to deliver other substances of different chemical composition, vehicles either of small or higher size, or complex structures, such as nanoparticles. Cell delivery peptides are usually coupled to other structures, as disclosed in state of the art, such as dendrimers, aptamers, stapled to macromolecular helices, etc.; the most widely used being micro- or nanoparticles, nanocarriers, polymers, scaffolds, or liposomes which would enhance stability, half-life and other pharmacokinetic properties of any drug or product delivered (Subramanian). Nowadays, therapeutic nanoparticles research is conducted to target the delivery of drugs more precisely, in order to improve their solubility, to extend their half-life, to improve efficacy, to reduce toxicity through enhancement of specificity and to reduce immunogenicity.

Nanoparticle targeting is particularly relevant to oncology applications, and to date therapeutic approaches take advantage of the passive accumulation of engineered nanoparticles in tumors because of the enhanced permeability and retention effect existing in tumors (Hamble & Hait). As above described, this accumulation is a passive, non-selective process that allows macromolecules of a certain size range to accumulate in the tumor. In contrast, the present invention shows that binding to our carrier peptides provides a more efficient active and selective transport crossing actively cell boundaries powered by cellular molecular motors.

Ligands conjugated to the surface of engineered nanoparticles can influence the mode of cellular internalization. As already disclosed in the state of the art, ligands to overcome cell membrane barrier such as folic acid, albumin and cholesterol, have been shown to facilitate uptake through caveolin-mediated endocytosis, whereas ligands for glycoreceptors promote clathrin-mediated endocytosis (Bareford). None of them have the dynamic capacity that the carrier peptides object of the present invention can render.

To evidence those properties, gold-tiopronin nanoparticles linked to the delivery peptides of the invention have been chosen, comparing to the same particles linked to a cell penetrating peptide that does not bind any cellular molecular motor as comparative control example. Gold nanoparticles of different sizes have been widely used because of lack of toxicity and easy elimination by renal clearance (Howard). Those nanoparticles can be fused to tiopronin or other molecules to improve nanoparticle stability and prevent aggregation as previously disclosed in the state of the art.

The present invention covers particular aspects of therapeutic nanoparticles, critical for their effective use, in which nanoparticles have been functionalized with the small peptide delivery sequences of the invention, which bind one of the protein components of the microtubule motor complex, preferably molecular motor dynein. By means of this new concept, the present invention shows that those functionalized nanoparticles are able to engage the microtubule dependent transport and become mobile, powered by cell molecular motors. By this active cellular transport, nanoparticles carrying any payload, acquire the property to move safely in the intracellular environment throughout the cytosol, in-and-out the cell nucleus and delivered from cell to cell beyond boundaries. Moreover, when peptides binding the microtubule motor complex of invention are bound to nanoparticles, the intracellular concentration of nanoparticles increased unexpectedly, as well as their dynamic properties and their capacity to be driven across intra- and inter-cellular barriers. Functionalized nanoparticles, powered by the delivery propeller peptides of the present invention, can enter and exit nucleus, spread through cell projections and cell to cell contacts, reaching neighboring cells with high efficiency as we show in examples.

DESCRIPTION OF THE INVENTION

Brief Description of the Invention

The invention relates to peptides binding to proteins from the microtubule motor complex, preferably, dynein-binding peptides, comprising the SEQ ID NO: 1 to 11 which are able to deliver molecules into cell, either in the cytoplasm, the nucleus or at inter-cell levels (cell to cell transport). Therefore, said peptides may be used in many technical fields comprising, among some others: diagnosis, therapy and pharmacology. Said peptides, some of viral origin, can mimic the ultimate viral mechanisms of cellular entry and transport as a whole, without the undesired effects of a viral vectors previously mentioned. These sequences have been identified by defining the minimal protein domain that interacts with the cellular transport machinery linked to microtubules. Therefore, the present invention surprisingly shows the dynamic properties of those peptides as carrier peptides for delivery, powered by intracellular molecular motor complex. The peptides of the invention allow rapid movement of the loaded substances, either inside the cell, across the cytoplasm, in-and-out the cell nucleus or from cell to cell, being the first consequence of its use as carriers, the boost of cellular uptake efficiency of the desired substances (for example drugs or pharmaceuticals) to be delivered.

The peptides of the invention are useful to deliver substances, such as nanoparticles. Therefore, the present invention covers particular aspects of therapeutic nanoparticles, critical for effective use, in which nanoparticles have been functionalized with the small peptide delivery sequences of the invention taken from a protein of viral or cellular origin, which bind the microtubule motor complex protein dynein. By means of this new concept, the present invention shows that those functionalized nanoparticles are able to engage the microtubule dependent transport and become mobile, powered by cell molecular motors. By this active cellular transport, nanoparticles carrying any payload, acquire the property to move safely in the intracellular environment through the cytosol, in-and-out the cell nucleus and are delivered across boundaries from cell to cell. Moreover, as described above for the propeller peptide bound to other peptides or chemical compounds, when it is bound to nanoparticles, the intracellular concentration of nanoparticles increased unexpectedly, as well their dynamic properties and their capacity to be driven across intra- and inter-cellular barriers. Functionalized nanoparticles powered by the delivery propeller peptide, included in the present invention, can enter and exit nucleus, spread through cell projections and cell to cell contacts reaching neighboring cells with high efficiency.

Preferred embodiments of the invention are detailed in the claims.

One of those embodiments are peptides binding to proteins which are components of the microtubule motor complex, preferably dynein-binding peptides, for their use in carrying and/or delivering substances to any required target, into any required cell compartment comprising the cytoplasm, the nucleus, the nucleolus, improving the carried/delivered substance capacity to be accumulated in the cell; crossing any cellular barrier and comprising cell-to-cell diffusion. Particularly preferred are protein-binding peptides comprising at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6.

The microtubule motor complex-binding peptides of the invention are particularly suitable for use in carrying and/or delivering organic substances preferably selected from: hormonal derivatives, growth factors, peptides, proteins, polymers, polysaccharides, enzymes, lipids, nucleic acids, drugs or pharmaceuticals; or inorganic substances preferably selected from: metals, gold, iron oxide or magnetic compounds. As a way of example preferred substances to be carried/delivered by the peptides of the invention are selected from: *Salmonella* Flagellin; anti-inflammatory drugs; analgesic drugs; interferons; cytokines; antibodies; antigens, preferably, hTERT, M2 of Influenza virus or CEA; antitumoral or chemotherapy agents, preferably, Leucovorin, Doxorubicin or hTERT inhibitor peptides; therapeutic agents or diagnostic tracers.

Another preferred embodiment of the invention are microtubule motor complex-binding peptides, such as dynein-binding peptides, linked to a structure selected from: nanoparticles, dendrimers, viruses, liposomes, micelles, scaffolds, lattices, surfaces or matrices, more preferably, a functionalized nanoparticle and more preferably a functionalized nanoparticle, linked to a microtubule motor complex-binding peptide, preferably to a dynein-binding peptide, wherein said protein-binding peptide comprises at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6.

In a further embodiment of the invention the above mentioned functionalized structures, particularly functionalized nanoparticles further comprise at least one adjuvant selected form: polymers, preferably PEG, protamine or avidin.

Another preferred embodiment of present invention are compositions, particularly pharmaceutical compositions, comprising a microtubule motor complex-binding peptide, such as a dynein-binding peptide, or a functionalized structure, preferably a functionalized nanoparticle, linked to a microtubule motor complex-binding peptide, preferably to a dynein-binding peptide, coupled to a substance to be delivered to any required target, into any required cell compartment comprising the cytoplasm, the nucleus, the nucleolus, improving the carried/delivered substance capacity to be accumulated in the cell; crossing any cellular barrier and comprising cell-to-cell diffusion. More preferred compositions, according to present invention comprise a microtubule motor complex-binding peptide, preferably a dynein-binding peptide, wherein said protein-binding peptides comprises at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6.

Preferred compositions according to present invention also may comprise a functionalized structure linked to a microtubule motor complex-binding peptide, preferably to a dynein-binding peptide, wherein said protein-binding peptide comprises at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6.

Among those pharmaceutical compositions of the invention, vaccine compositions are preferred, which comprise a microtubule motor complex-binding peptide, preferably a dynein-binding peptide, or a functionalized structure linked to a microtubule motor complex-binding peptide, preferably to a dynein-binding peptide, wherein said protein-binding peptides comprise at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6, the aforesaid peptide further coupled to an antigen to be delivered to any required target, into any required cell compartment comprising the cytoplasm, the nucleus, the nucleolus, improving the carried/delivered antigen capacity to be accumulated in the cell; crossing any cellular barrier and comprising cell-to-cell diffusion.

Also, other preferred pharmaceutical compositions according to present invention are antiviral composition, comprising a functionalized structure, preferably a functionalized nanoparticle, linked to a microtubule motor complex-binding peptide, preferably to a dynein-binding peptide, wherein said protein-binding peptides comprise at least one amino acid sequence represented by SEQ ID NO: 1 to 11, preferably having the amino acid sequence represented by SEQ ID NO: 1 to 11, more preferably comprising the amino acid sequence represented by SEQ ID NO: 6 and still more preferably having the amino acid sequence represented by SEQ ID NO: 6; said antiviral composition being able of being delivered to any required target, into any required cell compartment comprising the cytoplasm, the nucleus, the nucleolus, improving the capacity of the functionalized structure to be accumulated in the cell; crossing any cellular barrier and comprising cell-to-cell diffusion.

Finally, a further embodiment of present invention consists in the previously mentioned compositions for use in the prevention, treatment or diagnosis human or animal diseases selected, among others, from: cancer, infectious diseases, congenital diseases, tuberculosis, granulomata, bone diseases, osteoporosis, bone marrow diseases, nervous system diseases, neurodegenerative diseases, wound healing, burn repair or inflammatory diseases.

For the purpose of the present invention the term "comprise" or "comprising", all along present patent description, includes, specifically, the term "consisting" or "consisting of", when referred, particularly, to biological sequences. It means that the peptides of the invention may "comprise" any of the sequences listed in Table 1 along with other sequences or molecules or, in a preferred embodiment, the peptides of the invention may "consist of" any of said sequences listed in Table 1, the later case meaning that the peptides of the invention are precisely restricted to the fragment identified as such by the SEQ ID NO.

DETAILED DESCRIPTION OF THE INVENTION

Peptide sequences, according to present invention, binding the cell molecular motor dynein of viral and cellular origin, thus driving intracellular motion linked to microtubule motor complex, are shown in Table 1.

TABLE 1

| SEQ ID NO | SEQUENCE | NAME |
|---|---|---|
| SEQ ID NO: 1 | TASQT | Peptide 1 |
| SEQ ID NO: 2 | KSTQT | Peptide 2 |
| SEQ ID NO: 3 | KNTMT | Peptide 3 |
| SEQ ID NO: 4 | TTQNTASQT | Peptide 4 |
| SEQ ID NO: 5 | TVTTQNTASQT | Peptide 5 |
| SEQ ID NO: 6 | HPAEPGSTVTTQNTASQTMS | DynPro |
| SEQ ID NO: 7 | MSLLTEVETPIRNEWGSRSNGSSDPHPAEPGSTVTTQNTASQTMS | DynProM2 |
| SEQ ID NO: 8 | YTTQNTASQTMS | TransShort |
| SEQ ID NO: 9 | HPTEPYTTVTTQNTASQTMS | TransBA |
| SEQ ID NO: 10 | FPNPSGRSSEDKSTQTAG | TransRB |
| SEQ ID NO: 11 | PKDDKNTMTD | TransMy |
| SEQ ID NO: 12 | SLVSSDESVLHGSHESGEHV | Control peptide INTCT3 |

Figure 2:
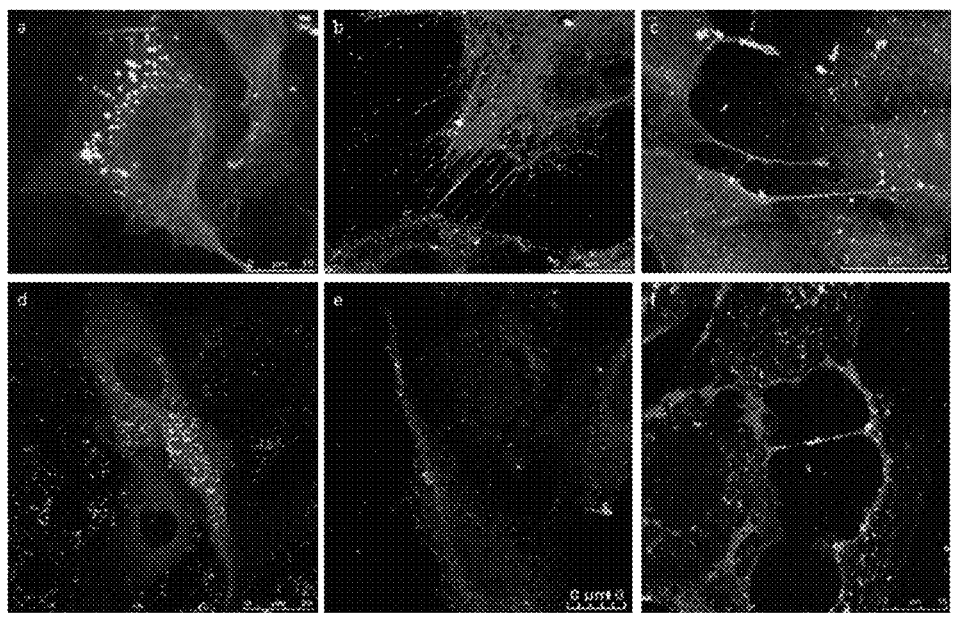

All peptides disclosed in Table 1, except SEQ ID NO: 12 (INTCT3) which is the comparative control, are microtubule motor complex-binding peptides. INTCT3 is a random amino acid sequence fused to a tail of 8 arginines which is a cell penetrating peptide (CPP) that does not bind any cellular molecular motor. All said peptides were assayed in the present invention with the purpose of illustrating and showing that any microtubule motor complex-binding peptide, and not only the peptides comprised in the Table 1, may be successfully used for carrying and/or delivering substances to any required target, into any required cell compartment, comprising cell-to-cell diffusion and delivery of the substance. Therefore, the present invention covers the use of any peptide that binds the microtubule motor complex, and/or any dynein-binding peptide for said purpose, and includes but is not limited to the peptides comprised in Table 1.

The microtubule motor complex-binding peptides assayed in the present invention were synthesized preferably at 95% purity. They may optionally comprise either a glycine (G) tail in the N-terminus or an arginine (R) tail in the C-terminus. In a preferred embodiment of the invention the glycine (G) tail may also comprises a Lysine (K) residue linked to (tetramethylrhodamine) TAMRA. In another preferred embodiment of the invention the peptides do not comprise the glycine (G) tail in the N-terminus, but they are linked to Rhodamine B.

These molecular motor propelled carrier peptides were able to transport with high efficiency any molecule or drug bound to them as we will show here.

Protein Rhodamine B was linked to the delivery peptide as a payload and added to Vero cells. Its movement was recorded by time-lapse videomicroscopy and compared to that of Rhodamine linked to control peptides with non-dynein binding peptide sequence (INTCT3 Internal control). The cellular uptake of Rhodamine B was very efficient and this fluorescent protein quickly accumulated in the cytoplasm of treated cells when it was linked to a dynein binding peptide such as DynPro (stands for Dynein Propelled; FIG. 1A a,c). DynPro was taken only as an example though other peptides binding dynein depicted in Table 1, presented similar properties, as TransRB (SEQ ID NO: 10) or TransBA (SEQ ID NO: 9), (FIG. 1A e,f). Rhodamine B or TAMRA fluorescence was found distributed and accumulated near the nucleus in the microtubule organizing center area (MTOC). Peptides were seen as red fluorescent dots moving rapidly following the movement of dynein along microtubules (FIG. 1A a,c). In contrast, cells treated with non-dynein binding peptide INTCT3 linked to Rhodamine B or TAMRA were found on the cell membrane or scarcely dispersed in the cytoplasm and the signal was lower after 18 hours post addition, even increasing 3 times the dose of control peptide added to the culture (because the absence of cellular retention of the protein fused to comparative non-dynein binding peptide or comparative control) (FIG. 1A b,d) than the signal observed using DynPro. Rhodamine B/TAMRA linked to dynein binding peptides was observed inside cells from the first minutes after adding the peptide to cultures and it was accumulated timely wise, as proven by the increasing fluorescent signal inside cells (FIG. 1B). Peptides represented by amino acid sequences SEQ ID NO: 1-11, all them showed similar intracellular distribution and dynamic properties.

Time lapse videomicroscopy unrevealed a high speed movement of rhodamine B linked to the carrier peptide. Its intracellular movement allowed a quick transport of the molecule from the cell periphery towards the perinuclear zone at the MTOC (FIG. 1A a,c). Also it was possible to observe bidirectional movement toward cell projections and intercellular transport along cell to cell contacts (FIG. 1C b-d arrow head). This highly efficient movement, spread and intercellular transmission was never reported before in the state of the art. The same experiments were performed using tetramethyl-rhodamine (TAMRA) instead of rhodamine B, obtaining identical results. Diverse peptide formulations in Table 1 were tested obtaining similar results. However, DynPro was preferred because of its solubility properties and easy use.

Different cell lines from diverse species were tested: human, monkey, canine, hamster, insects etc., and from different tissue origins, as a mode of example: fibroblastic, epithelial, neurons, macrophages, lymphocytes and also transformed or tumor cell lines as those from cervical uterine carcinoma or neuroblastoma. Dynein-binding peptides exhibited the same properties in all cell types irrespective of the species, tissue origin and/or transformed or tumoral cell status (FIG. 1C a-d).

To emphasize how those peptides dynamic properties rely in microtubule dependent movement we analyzed microtubules in peptide treated cells with different methods to show colocalization with these structures. In cells transfected with alpha-tubulin-GFP and/or stained for microtubules with marked antibodies, carrier/delivery peptides of present invention showed colocalization with microtubules. Rhodamine bound to the carrier peptide moved using microtubule dependent transport towards the nucleus and cluster at the microtubule organizing center or MTOC (FIG. 2). Dynein favors cell polarization towards the periphery and intense accumulation of the carrier peptides of invention was found in cell extensions; either laminar extensions called lamellipodia and/or fine projections called filopodia and passing through cell to cell connections therefore proving that the peptides of the invention traveled from cell to cell (FIG. 2). Rhodamine B protein linked to delivery peptide was actively transported through cell-cell junctions and connections such as adherent cell-to-cell junctions (as a way of example in epithelial cells), filopodia and other cell processes and extensions, such a nanotubes, uropods, podosomes, etc. . . . . This pumping out of the protein resulted in quickly spread between cells all over the cell culture.

The peptides of invention colocalized with microtubules, anti-dynein light chain antibodies (anti-DLC8 antibody raised in rabbits) and run in parallel with other microtubule motor complex chains, such as intermediate chain as shown using specific anti-intermediate chain antibodies (FIG. 2e). Rhodamine intracellular localization was analyzed and high percentage of colocalization was found with a lectin marker (wheat germ agglutinin; WGA) which distributes widely on membranes and endosomes. Furthermore, this marker stained cell-cell junctions and connections, where the peptides were found colocalizing with WGA, as they traveled from cell to cell (FIG. 2f).

The evidence of this cell to cell transport of the protein delivered by the carrier peptides of the invention, shows the ability to spread any protein of interest to a high number of cells. As this spread remains intracellular, it increases cellular retention of the compound delivered and avoids losses or leakage of the protein which could in turn allow lowering initial dosage of any candidate protein to be transported. This property of the carrier/delivery peptides of invention would make it especially favorable for distribution in secluded or scarcely vascular compartments. Also, it reduces exposure of the compound to the extracellular environment which could benefit the biodistribution of a determined compound to be transported and eventually help to the compound "stealthing", in order to reduce its recognition by the immune system and its potential immunogenicity against the carrier itself.

In parallel, a non-motor binding control peptide (INTCT3) was assayed in each experiment which showed lower signal even increasing 3 times its initial concentration. It remained at cell periphery and scarce peptide signal was seen inside cells lacking the fast movement recorded with dynein-binding peptide (DynPro). INTCT3 lacked also the property to accumulate and/or trafficking from cell to cell (FIG. 1Ac, d).

Figure 3:
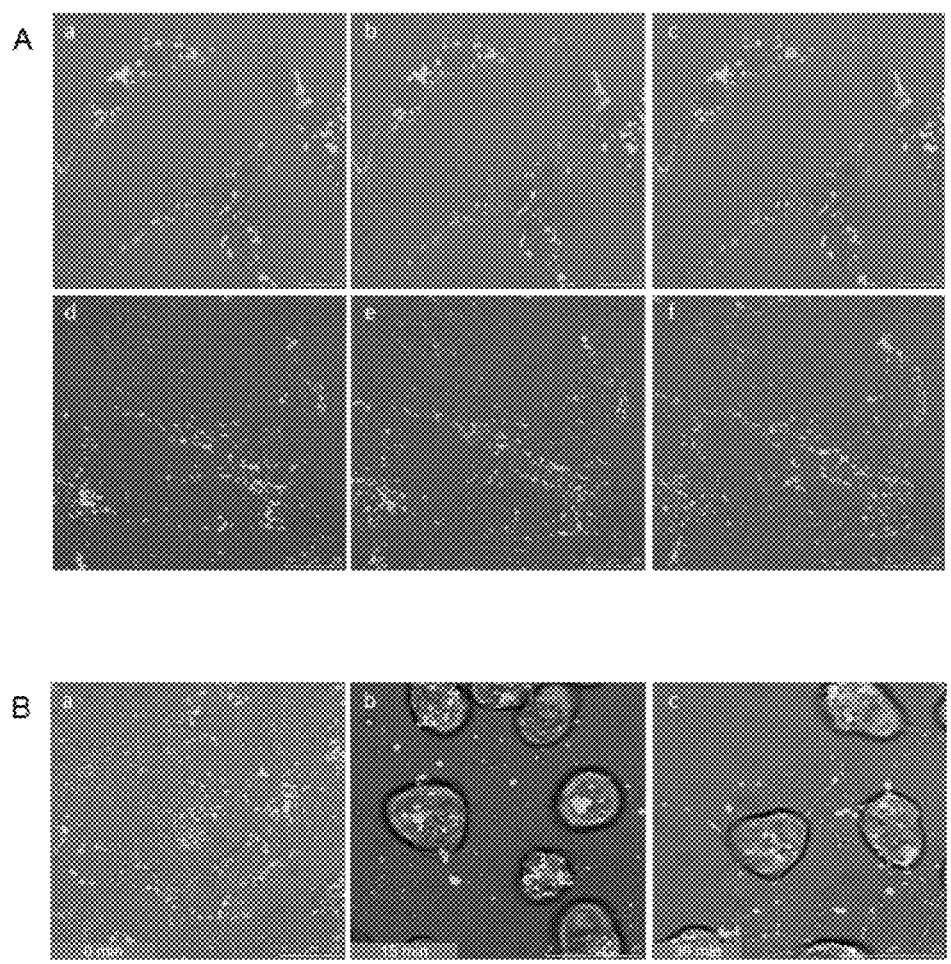

Delivery peptides transport was shown to be dependent on microtubules as correspond to the microtubule motor dynein dependent movement. The present invention shows how transport can be stopped with microtubule depolymerizing drugs as Nocodazole and after washing out the drug, the transport was recovered (FIG. 3). Nevertheless, other drug agents depolymerizing actin cytoskeleton (LatrunculinA or Jasplakinolide) did not inhibit this movement because dynein dependent transport is not actin dependent.

Figure 4:
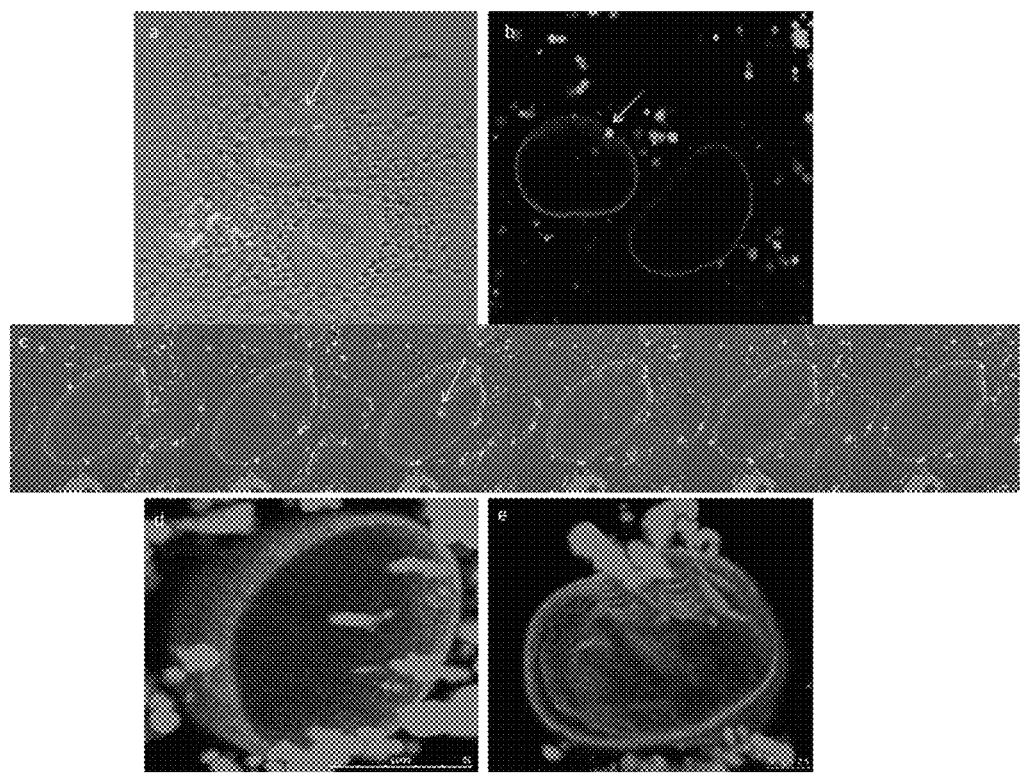

Another particular interest of the transport linked to dynein-binding peptides is that they deliver loads across the nuclear membrane in and out the nucleus (FIG. 4). This relies on the property of dynein to interact dynamically with the nuclear envelope allowing assembly and reassembly of nuclear lamina. It has been found that the carrier peptides of present invention could transport the protein Rhodamine across the nuclear envelope and the nuclear lamina as shown in cells transfected with lamin B1-GFP (FIG. 4).

Figure 5:
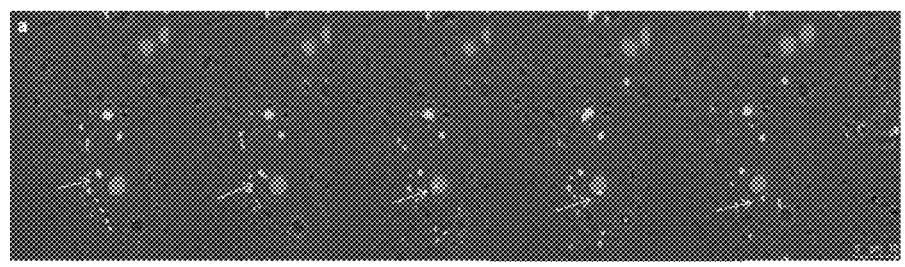
Figure 5:
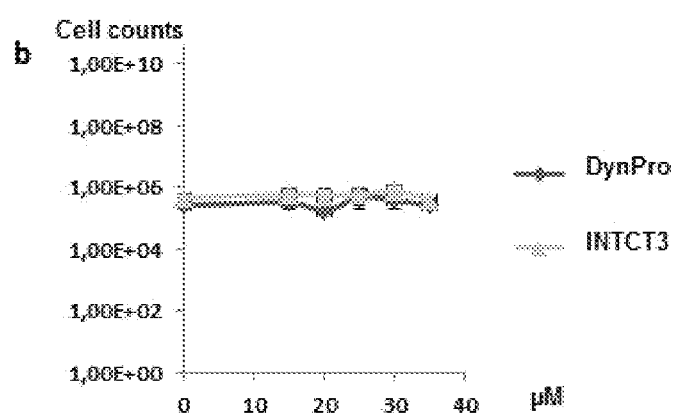
Figure 5:
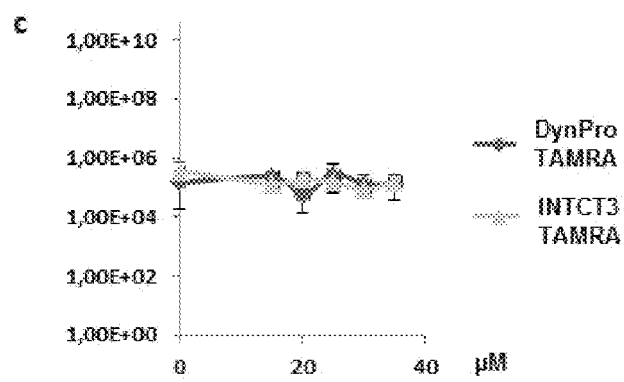
Figure 5:
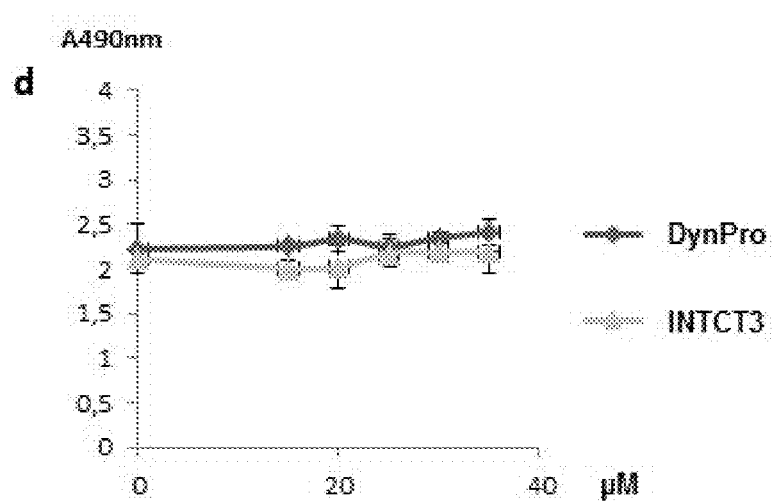
Figure 5:
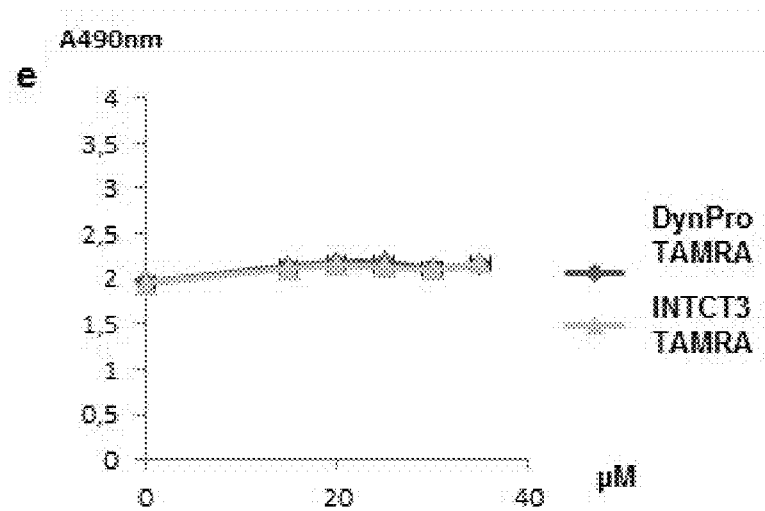

Then, the delivery peptides of the invention were able to cross nuclear envelope to get into the nucleus. They accumulated in the nucleolus or enter this organelle, move around and exit again (FIG. 5a). The use of the carrier peptides of present invention overcomes the limitation of nuclear localization signal NLS peptides which may deliver molecules to the nucleus but within the strong limitation of the nuclear pore size. Another limitation linked to such a specific targeting has been recently suggested as some gene therapy protocols were less efficient than expected because the delivered product remains retained inside nucleus. This circumstance, as mentioned before, will not occur with the carrier peptides of present invention. Neither cell viability nor cell proliferation modifications were found with any peptide formulation of present invention (FIG. 5 b-e).

Figure 6:
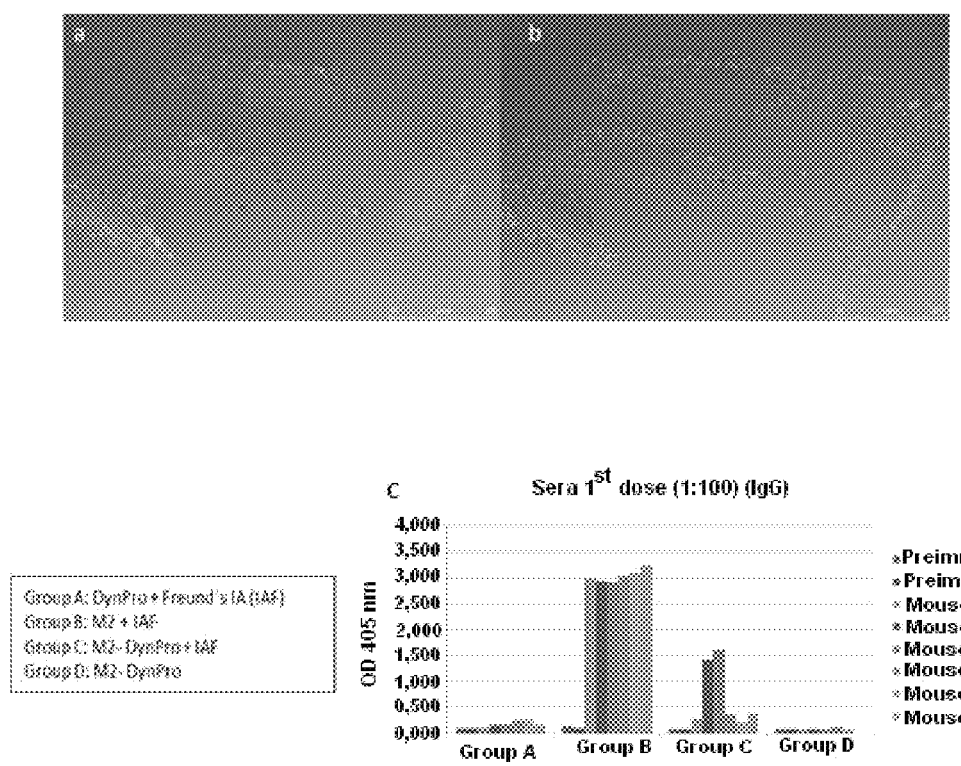
Figure 6:
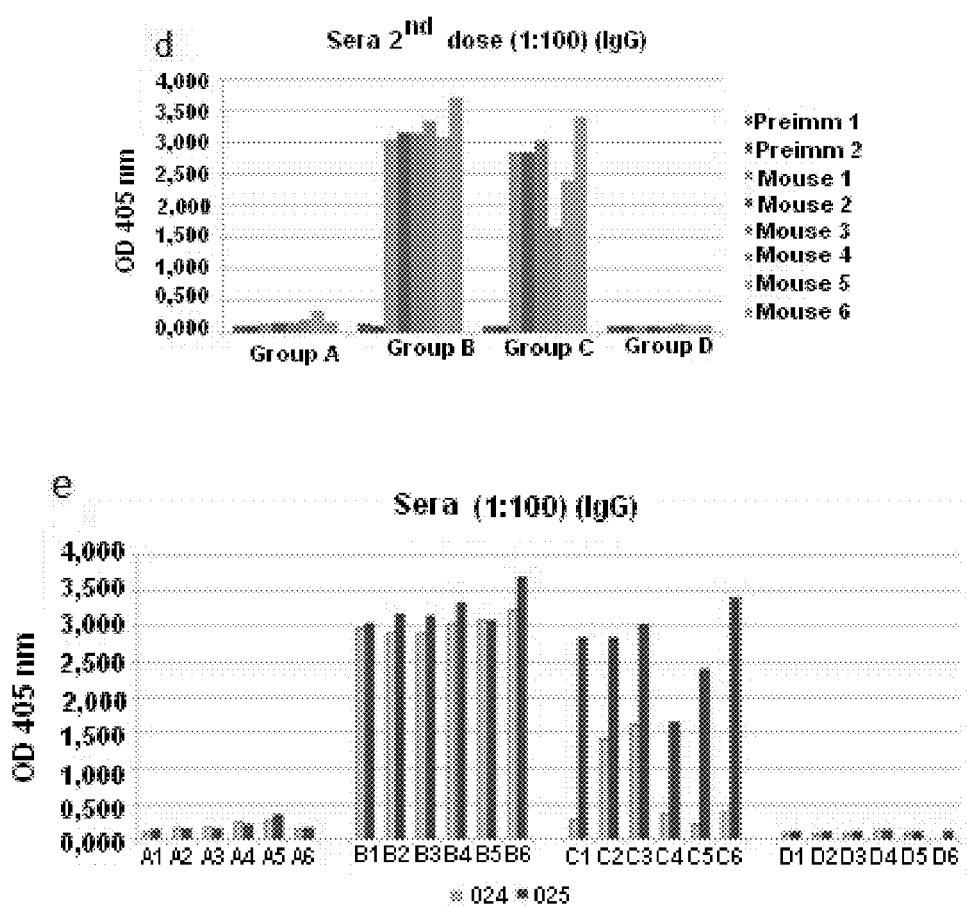

Also, it was assayed the transport of M2 influenza antigen as payload, bound to the carrier peptide DynPro (FIG. 6). M2 influenza antigen has been used in the state of the art as an Influenza vaccine, but in the present invention we used M2 influenza vaccine fused to the carrier peptide object of the present invention. We show that M2 influenza antigen's intracellular distribution and movement was coincident with that of the carrier peptide of invention, retaining, once delivered, the same antigenic properties, as it is demonstrated by using a rabbit antibody against M2 influenza antigen (FIG. 6*a*). This shows the ability of the carrier peptides of invention to deliver many other antigens as vaccines. The state of the art offers many possibilities in this regard, including protein subunits or DNA vaccines. Antigens can elicit an immune response against any infectious agent and are used in vaccination. Also, tumor antigens are currently used as anticancer vaccines. In Example 5, M2 influenza antigen was also fused to nanoparticles functionalized with the delivery peptides of invention and, once administered to mice, a specific antibody response was observed, as depicted in FIG. 6. Inoculations in mice have been carried out with M2 peptide bound to one of the carrier peptides of invention (DynPro) and elicited specific antibody immune response to Influenza virus M2 antigen, was observed, when fused to the propeller peptide either with or without adjuvants (FIG. 6 *c-d*). Mice remained asymptomatic and healthy, stable in weight and temperature along the experiment.

It was also assayed how the peptide carriers of invention are useful to deliver higher size and complexity structures such as nanoparticles (FIG. 7). For that purpose we used these delivery peptides to functionalize Gold-Tiopronin nanoparticles (Au@tiopronin, Fluka, Germany) with tetramethyl-rhodamine (TAMRA) as a payload (FIG. 7*a*). We selected gold-tiopronin nanoparticles because they are able to be further fused to any drug or chemical compound to be transported. Functionalization of gold nanoparticles with cell penetrating peptides has been performed before, for example with Tat peptide. Tat peptide although can drive the nanomaterials into the cell, shows low efficiency. The term "functionalization", for the purpose of present invention, refers to the addition of functional groups onto the surface of said "structure", a nanoparticle a way of example, preferably by chemical synthesis methods, which were able to couple to the peptides of invention. This would be equivalent to install a motor or propeller (one peptide of invention) in a boat (any nanoparticle), for force generation and movement. Then, the power-boat can be loaded with different drugs (chemical compounds, pharmaceuticals) to be carried. As an example, tiopronin, a pharmaceutical drug used in renal diseases, has been used.

In the present invention is disclosed a simple production procedure of water-soluble and stable gold nanoparticles functionalized with the dynein-binding peptides of invention, the nanoparticles thus functionalized can be ferried very efficiently into the cell, even into the cell nucleus. Au@tiopronin nanoparticles have been prepared using the procedure of Murray et al. (Templeton). These nanoparticles comprise a gold cluster stabilized with the non-natural aminoacid tiopronin (N-2-mercaptopropionylglycine). Tiopronin has a free terminal —$CO_2H$ group allowing us to functionalize the gold nanoparticles with the peptidic sequences. The reaction was executed in a methanolic/acetic acid mixture. Codissolution of $HAuCl_4$ and tiopronin gave a stable ruby-red solution. Acidic conditions at this point are very important to guarantee the protonation of tiopronin carboxylic groups, and provide an efficient and dense self-assembling monolayer of tiopronin protecting the gold nanoparticles. The addition of $NaBH_4$ reductant provided a dark solution by reduction of the gold salt and formation of the nanoparticles. The obtained nanoparticles were water-soluble and stable in physiological conditions. The excess of tiopronin and salts were removed by dialysis and characterized by UV/Vis and Transmission Electron Microscopy (TEM). TEM images showed a mean diameter of 2.8 nm for the gold core of the Au@tiopronin nanoparticles. The UV/Vis absorption spectra showed and almost non-detectable surface Plasmon band (SPB) as consequence of the small size of the clusters. Further functionalization of the nanoparticles with aminated molecules, such as tiopronin, has been carried out using the procedure described in Example 5. The resultant nanoparticles were analyzed by Zeta potential, UV/Vis, fluorescence and mass spectroscopy (MS), showing that the carrier peptides of invention were incorporated to the nanoparticles which showed non-aggregation of the cluster, after peptide coupling.

As control, we used first plain Gold-Tiopronin-nanoparticles carrying tetramethylrhodamine TAMRA with no peptide functionalization. In this case signal was very low even increasing the dose and few nanoparticles were internalized into cells along the first three hours of incubation. As a second control, gold-tiopronin nanoparticles were functionalized with a non-dynein binding peptide (INTCT3). These other control nanoparticles stayed mostly at the cellular membrane drawing cell contour. Very few were internalized and those were observed dispersed in the cytoplasm, not in the nucleus.

In contrast, cellular motor-powered nanoparticles and their payload, such as Au@tiopronin nanoparticles functionalized with a dynein binding peptide were efficiently accumulated inside cells and enriched at the perinuclear area (FIG. 7 b-c) and retained all properties above described for the delivery peptides; such as intra and intercellular distribution, accumulation properties, intranuclear distribution and rapid transfer through cell to cell contacts. Gold-Tiopronin nanoparticles functionalized with a dynein-binding peptide loaded with TAMRA (p.e. Au@TioproninDynPro) were rapidly internalized and presented a fast movement across the cytoplasm, to cell projections and circulated from cell to cell spreading through cell-cell junctions (FIG. 7c).

Figure 7:
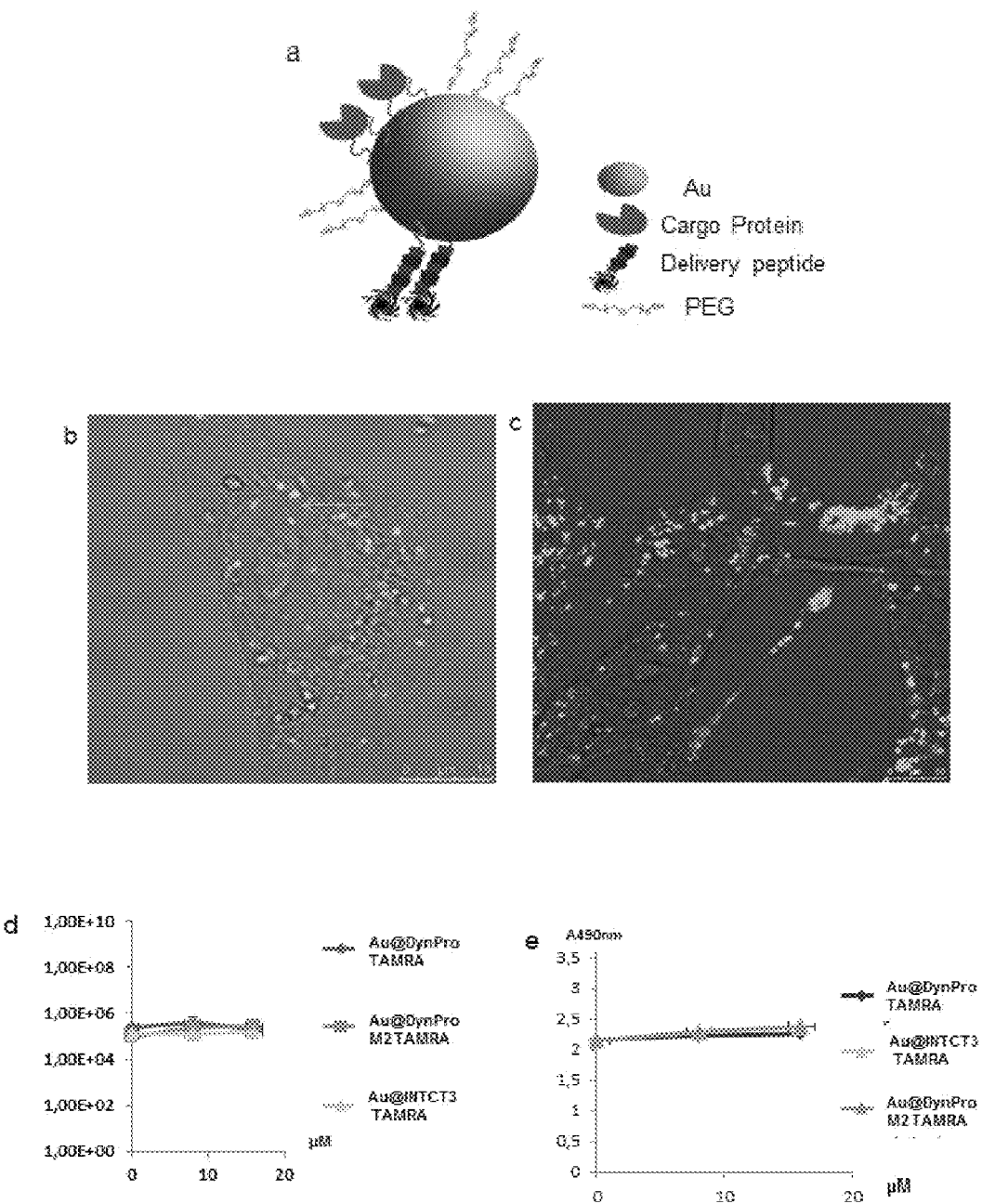

Also, these nanoparticles crossed the nuclear envelope, moved inside the nucleus to the nucleolus (FIG. 7b). The bigger size of the nanoparticles allowed seeing an imprint of their movement along the nucleus that was physically evident using bright field microscopy as linear protrusions. These "worm-like" tracks were observed as the nanoparticles moved through the nuclear area (arrows FIG. 7b). Neither cell viability nor cell proliferation modifications were found with nanoparticles functionalized with any carrier peptide formulation of the invention (FIG. 7 d-e).

The extraordinary properties of these dynein-binding peptides functionalized nanoparticles made them especially appropriate to load any type of compound, drug or chemical and achieve the desired requirements of intracellular delivery to all compartments, reaching the cell nucleus. Those characteristics, together with their intracellular accumulation capacity would, in turn, allow reductions on administration doses of a given drug because of its better biodistribution. Moreover, the quick spreading of these motorized nanoparticles between cells, remaining intracellular, reduces exposure of any given element transported to the extracellular environment, hence, minimizing eventual immunogenicity. This overcomes an extended problem found with viral vectors in gene therapy or vaccination: the elicitation of an immune response against the viral vector or undesired reactions against the fetal calf serum (FCS), as those viral vectors are obtained, at high titers, in cell cultures containing FCS (Bao, Moffat).

There are a handful of applications of the delivery system object of the present invention. In one preferred embodiment of present invention, it has been increased size and stability of the nanoparticles by fusing Polyethylene glycol (PEG), a polymer of ethylene oxide, with many applications in pharmaceutics and medicine. It is relevant to show how those PEGylated nanoparticles, coupled to the carrier/delivery peptides of invention, were internalized and accumulated in cells very efficiently to the nucleus and were transported from cell to cell diffusing very rapidly along the cell culture despite of their bigger size (FIG. 7a).

This cell-cell diffusion ability becomes more crucial in drug delivery in some infectious diseases in which the infectious agent is intracellular (*Salmonella, Listeria*, viral diseases), or pathologies difficult to access in a secluded or less vascularized environment such as: tuberculosis, granulomata, bone disease, especially osteoporosis treatments, bone marrow, nervous system. In the field of infectious diseases, the carrier/delivery peptides of invention would be able to spread very quickly to antigen presenting cells.

Dynein-binding powered nanoparticles are especially suited for nervous system delivery. Axonal dynein is very active carrier along axons. We have demonstrated that we could take advantage of its movement with the dynein-binding delivery peptide in cell lines of neural origin (FIG. 1C c-d). Any molecule bound to axonal dynein would quickly spread through both central and peripheral nervous system depending on the site of injection. Current anti-inflammatory and analgesic drug treatments, used in pain therapy, sometimes are administered intramedullarly. Those drugs bound to motorized nanoparticles could lower anti-inflammatory dosage, expand time of pain relapse. Other treatments of neurodegenerative diseases, Parkinson, Alzheimer, etc. could benefit of the efficient delivery of drugs using the carrier/delivery system of the invention.

Molecular motor powered nanoparticles would be a useful method to deliver gene therapy agents, instead of using viral vectors (adenovirus, retrovirus), which have the previously mentioned undesired side effects. Molecular motor powered nanoparticles could substitute the use of viruses as vectors and use instead the moieties that virus use to be transported in the cell and reach the nucleus, namely the dynein-binding domain of a viral protein.

One clear application of motorized nanoparticles of the invention would be the increase in the biodistribution of any chemical or drug. Analgesic or anti-inflammatory drug treatments would be more effective if delivered by the system of invention, thus allowing to lower dosage and side effects. To facilitate its wide spectrum of use, we would include an avidine residue in the motorized nanoparticles. Those would be Fit-for-purpose Motorized Nanoparticles by design, being able to transport any compound, chemical or drug linked to the protein biotin and to incorporate it to the nanoparticles in one "clic" (one step chemical reaction because of the natural affinity of biotin for avidin, FIG. 7a). Chemicals or drugs to be transported include hormonal derivatives, enzymes peptides, proteins, enzymes, antigens, lipids, sugars, nucleic acids and any other organic or inorganic molecules, for either therapeutic or diagnostic use. The field of application could be infectious diseases, metabolic diseases, tumors, etc. because this method to deliver drugs, increase efficacy and simultaneously lower side effects by optimizing distribution, delivery and transport where is needed, that will allow, in turn, to lower the doses to be administered and undesired side effects.

This would be a crucial objective for anticancer treatments. Then, we have demonstrated delivery of the antitumoral agent Leucovorin linked to Au@tiopronin nanoparticles functionalized with the dynein binding peptide (DynPro). Based in the same principle, chemotherapy drugs delivered with motorized nanoparticles would optimize chemotherapeutic agent's accumulation in tumour cells and it would permit lower active dose administration and minimize side effects.

Also there is a wide field of application in diagnosis. The motorized nanoparticles of invention could be applied to deliver diagnostic tracers into any cell organ or tissue. Motorized nanoparticles fused to targeting molecules can be useful tools in diagnostic detection systems including imaging systems, for example of tumours in early diagnosis of micrometastasis. We have developed nanoparticles expressing tumour antigens such as carcinoembrionic antigen (CEA) or human Telomerase (hTERT). Those systems could be used in anti-cancer vaccination trials.

Also, a specific anticancer treatment can be developed by fusing a human telomerase (hTERT) inhibitor peptide to the molecular motors powered nanoparticles of present invention. As the state of the art indicates, this sequence is effective when expressed in cancer cells. PinX1 and its small TID domain bind the telomerase catalytic subunit hTERT and potently inhibit its activity (Zhou). It has been called liver-related putative tumor suppressor (LPTS). Also, it has been demonstrated its antitumor activity (Liao). In the present invention we have incorporated the hTERT inhibitor peptide to the motorized nanoparticles which constitutes a completely novel approach in this cancer therapy. This will circumvent the problem of many anticancer therapies that only reach parts of the tumor because the poor and abnormal vascularization of tumor cells. Motor powered nanoparticles of the invention would enhance diffusion of any drug or anticancer moiety bound to them and would potentiate accumulation in tumor cells.

Similarly, by fusing the antigen, the human telomerase (hTERT) peptide, to the molecular motors powered nanoparticles of invention; an enhanced spreading anticancer vaccine is developed.

Dynein and associated proteins function also in cell polarization, migration and growing, facilitate fibroblast migration. Accordingly, the dynein binding peptides object of the present invention, based in its unique properties would be useful, either by themselves alone or by potentiating chemicals, drugs or growth factors used in wound healing, to accelerate burn healing, thus facilitating tissue repair.

Also, dynein is involved in the growth cone formation in neurons. Then dynein-binding peptides of the invention would be useful then to deliver and to stimulate nerve growth. Hence they could be applied by themselves alone or in combination with other drugs or nerve growth factors in peripheral nerve or spinal cord injury, stimulating growth and tissue repair processes.

Therefore, the first embodiment of the present invention refers to peptides binding a protein from the cell microtubule motor complex, such as dynein for using in carrying and/or delivering substances to any required target, into any required cell compartment, comprising cell-to-cell diffusion. In a preferred embodiment of the invention the dynein-binding peptide comprises any of the amino acid sequence represented by SEQ ID NO: 1 to 11.

Peptides from the present invention show the main common feature of being able to "hijack", bind or engage this natural cellular transport system through binding one of this proteins of the microtubule motor complex.

For the purpose of the present invention the term "substance" refers to any matter which can be delivered by the motor protein-binding peptides of the invention, for example (non-exhaustive list): organic substances preferably selected from hormonal derivatives, growth factors, peptides, proteins, polymers, polysaccharides, enzymes, antigens, lipids, nucleic acids, drugs, pharmaceuticals, *Salmonella* Flagellin, anti-inflammatory drugs, analgesic drugs, interferons, cytokines, antibodies, antitumoral or therapeutic agents, diagnostic tracers, antitumoral agents Leucovorin or hTERT inhibitor peptides, antigens hTERT, M2 of Influenza virus or CEA; or inorganic substances preferably metals, gold, iron oxide or magnetic compounds.

Moreover, for the purpose of the present invention, the wording "cell compartment" refers to the location where said "substances" may be efficiently delivered, comprising all closed parts within a cell, whose lumen is usually surrounded by a single or double lipid layer membrane, particularly the nuclear compartment comprising the nucleus, and the nuclear envelope, organelles, and cytosol, and more particularly the nucleolus, vesicles, vacuoles, centriole, and also the cell-to-cell junctions and connections.

Another embodiment of the present invention refers to a structure functionalized with a motor protein-binding peptide. The term "structure" refers to any entity to which the peptides of the invention may be linked, for example: nanoparticles, dendrimers, viruses, liposomes, micelles, scaffolds, lattices, surfaces or matrices. In a preferred embodiment of the invention, the present invention refers to nanoparticles functionalized with a dynein-binding peptide which preferably comprises the SEQ ID NO: 1 to 11. Said nanoparticles may further comprise adjuvants preferably PEG, other polymers, protamine or avidin.

Moreover, for the purpose of the present invention, "functionalization" means any surface modification, that is, the act of modifying the surface of a material by bringing physical, chemical or biological characteristics, different from the ones originally found on the surface of said material. This modification is usually made to solid materials, but it is possible to find examples of the modification to the surface of specific liquids. The modification can be done by different methods with a view to altering a wide range of characteristics of the surface, such as: roughness, hydrophobicity, surface charge, surface energy, biocompatibility and/or reactivity between others.

Another embodiment of the present invention refers to pharmaceutical composition comprising a peptide with the ability of binding to a protein from the microtubule motor complex, such as dynein, or a structure functionalized linked to a peptide with the ability of binding to a protein from the microtubule motor complex, such as dynein, in both embodiments, coupled to at least a substance to be delivered to any required target, into any required cell compartment, comprising cell-to-cell diffusion. In a preferred embodiment, the structure functionalized with a peptide with the ability of binding to a protein from the microtubule motor complex, is a nanoparticle. In another preferred embodiment of the invention, the pharmaceutical composition comprises a dynein-binding peptide that comprises the SEQ ID NO: 1 to 11, or a structure functionalized linked to a dynein-binding peptide that comprises the SEQ ID NO: 1 to 11, coupled to a substance to be delivered to any required target, into any required cell compartment, comprising cell-to-cell diffusion.

The above pharmaceutical composition may be a vaccine composition comprising a peptide with the ability of binding to a protein from the microtubule motor complex, preferably a dynein-binding peptide that comprises the SEQ ID NO: 1 to 11, or a structure functionalized linked to a dynein-binding peptide that comprises the SEQ ID NO: 1 to 11, in both embodiments, coupled to an antigen to be delivered to any required target, into any required cell compartment, comprising cell-to-cell diffusion; or an antiviral composition comprising a structure functionalized linked to a dynein-binding peptide that comprises the SEQ ID NO: 1 to 11, to be delivered to any required target, into any required cell compartment, comprising cell-to-cell diffusion.

The scope of diseases which can be treated, diagnosed or prevented with the pharmaceutical composition of the invention directly depends on the actual substance delivered by the peptides of the invention. Since, as cited above, either organic or inorganic substances can be delivered, a wide scope of diseases can be treated, diagnosed or prevented with the pharmaceutical composition of the invention, for example (non-exhaustive list): cancer and other malignancies, infectious diseases, tuberculosis, granulomata, bone diseases, osteoporosis, congenital diseases, enzymatic defects either acquired or hereditary, endocrine diseases, autoimmune diseases, bone marrow diseases, nervous system diseases, neurodegenerative diseases, pain treatment, wound healing, burn repair or inflammatory diseases.

Therefore, the present invention also refers to a method for the prevention, treatment or diagnosis of all said possible diseases which comprises the administration to the patient of an effective amount of the above cited pharmaceutical composition. Any suitable route of administration can be used for administering the pharmaceutical composition of the invention to the subject, being the preferred routes of administration intravenous, intramuscular, intradermal, oral, intranasal, topical, intramedullar or intrathecal in nervous system and intratumoral in the particular case of solid tumors. Moreover the pharmaceutical composition may comprise any excipient, known in the state of the art, including other carriers for the active drug. Said excipient will be elected depending on the route of administration actually used.

BRIEF DESCRIPTION OF THE FIGURES

FIG. 1

A. Cellular uptake efficiency of a protein propelled by the cargo delivery peptide. Localization of peptides binding microtubule motor complex protein dynein versus non-motor protein binding control. 1A a, c: Cellular uptake of cargo protein Rhodamine linked to DynPro (Dynein propelled) peptide is seen as dots distributed in the cytoplasm (5 μM). 1A b,d: Rhodamine linked to INTCT3 control peptide in culture plated Vero cells after 18 h exposure to the peptides. 1A e: Other sequences binding a protein from the microtubule motor complex. Cellular accumulation after incubation of Vero cells with TransRB peptide. 1A f: Cells incubated with TransBA. The subcellular distribution and dynamic properties of all dynein-binding sequences tested was the same with all dynein-binding peptides.

B. Dynein-binding peptides cluster at the perinuclear area, close to the microtubule organizing center (MTOC; FIG. 1B c arrow) following the movement of dynein motor protein linked to microtubules. 1B a-c: Progressive timely accumulation of Rhodamine when linked to dynein-binding peptide in culture plated Vero cells after 30-120 min incubation with peptides. 1C a,b: HEK293T cells after 1 hour incubation with dynein-binding peptide. 1C c,d: Human neuroblastoma cell line SK-N-MC after 1 h incubation with peptide. Peptide moved rapidly across the cytoplasm and from cell to cell (arrowheads). Dynein-binding peptides displayed same subcellular distribution, inter cell transport ability and dynamic properties in a wide range of cell types tested.

FIG. 2. Molecular motor protein dynein-binding peptides deliver loads from cell to cell. Rhodamine protein linked to the carrier/delivery peptides of invention is actively transported through cell-cell junctions and connections by adherent junctions, filopodia and cell processes. This pumping out of the protein makes it quickly spread between cells all over the cell culture. 2*a*: Cell entry movement following a microtubule tract. 2 *b-f*: Spread of peptide through cell-to-cell connections and projections. Figure shows Vero cells after incubation with 10 μM delivery peptide DynPro counterstained with 2 *a-c*: an antibody anti dynein light chain (DLC8) 2*d*: anti-tubulin antibody 2*e*: (dynein intermediate chain) antibody which is another dynein chain forming part of the microtubule motor complex together with heavy, light intermediate and light chains. 2*f*: with wheat germ agglutinin (WGA-488), that labels cell surface, cell-cell contact and processes.

FIG. 3. Delivery peptide rapid movement is a microtubule associated movement.

3A a-c: Delivery peptide transport movement was abolished by adding a microtubule depolymerizing drug to culture media, 2.5 μM Nocodazole for 30 min (3Aa: 0 sec, b: 4 sec, c: 8 sec). 3Ad-f: Then, media was removed and, after washing, delivery peptide movement was recovered and delivery peptide continued spreading protein rhodamine in cells (3Ad: 8 sec, 3Ae: 16 sec, 3Af: 24 sec). 3B: In contrast, actin depolymerizing drugs produced noticeable cell shrinking because of collapse of actin cytoskeleton, but transport was preserved and delivery peptide was recorded moving along cells and remaining projections (LatrunculinA 0.1 µM) 3Ba: No drug, 3Bb: after 15 min drug incubation, 3Bc: 30 min. 10 µM DynPro was added to vero cells and 30 min after, media containing cytoskeleton depolymerizing drugs were added.

FIG. 4. Dynein-binding peptides are able to deliver loads across the nuclear membrane. 4a: Delivery of rhodamine across the nuclear membrane is seen as tracks of peptides inside the nucleus. 4 b-c: Nuclear envelope stained with laminB1-GFP. 4b: nuclear envelope appears discontinued when peptides are crossing through it. 4c: Subsequent frames of videomicroscopy showing peptides crossing nuclear envelope and nuclear envelope wrinkles as the sites of peptide disruption are reorganized. 4d: Tridimensional reconstruction of the nuclear envelope shell showing peptides entering the nucleus. 4e: Nuclear envelope wrinkles in sites of entry. The figure depicts vero cells transfected with laminB1-GFP and treated with 10 µM DynPro peptide.

FIG. 5. Dynein-binding peptides deliver loads in the nucleolus. 5a: Time lapse videomicroscopy 1 frame/sg of Vero cells transfected with nucleolin B3-GFP after 1 h incubation with 10 µM DynPro. Arrows show delivery peptide trafficking in and out the nucleolus stained with nucleolin. 5 b-c: Cell viability was not affected with increasing doses of dynein-binding peptide or control by themselves or linked to TAMRA. 5 d-e: Cell proliferation was not modified with increasing doses of dynein-binding peptide or control by themselves or linked to TAMRA.

FIG. 6. Dynein-binding peptide delivered antigen elicit an efficient antibody immune response. 6a DynPro peptide loaded vero cells linked to M2 influenza antigen. 6b: With an antibody recognizing influenza M2 antigen, it was possible to detect in the same cells the delivery and wide intracellular distribution of the antigen. 6 c-e: Antibody response elicited by the different peptide and control preparations in mice (Preimm), after first and second inoculation. Group A: 2 µg DynPro with Freund's Incomplete adjuvant (IAF). Group B: 2 µg M2 with IAF. Group C: 2 µg M2-DynPro with IAF. Group D: 2 µg M2-DynPro. 6e: Comparison of the ELISA IgG titers obtained in the different mice groups inoculated with peptide preparations and controls. X axis displays each animal from each group at first (grey bars) and second inoculation (black bars).

FIG. 7. Nanoparticles functionalized with dyneine-binding peptide. 7a: Scheme of nanoparticle structure; delivery peptide motor properties act as a propeller for the Au-tiopronin nanoparticles. This type of structure is able to carry diagnostic tracers (TAMRA), polymers (PEG), antigens and other chemical compounds. 7b: Au-tiopronin-TAMRA nanoparticles functionalized with dynein-binding delivery peptide DynPro were incubated with Vero cells for 1 hour. Arrow: Nanoparticle entering the nucleus made an imprint visible with phase contrast along its path because of its bigger size. 7c: Au-tiopronin-TAMRA nanoparticles functionalized with dynein-binding delivery peptide incubated for 2 h. Rhodamine accumulation is visible in the cytoplasm and cell-cell projections. 7 d-e: Cell proliferation was not modified with increasing doses of the different nanoparticle formulations.

FIG. 8.
  A. Dynein-binding domain of myosinV, TransMy. Single-molecule videomicroscopy disclosed that these peptides enter the nucleus by nuclear envelope remodeling, shuttle across the nuclear envelope and reach the nucleolus in Vero cells and other cell types.
  B. Gold nanoparticles were functionalized with TransMy as a tool for gene/drug delivery into the cell cytoplasm and the nucleus. The nanoparticles prolong the peptide bioavailability and confer stability, biocompatibility and no toxicity having no adverse effect on viability or cell orphology. They also allo detection by electron croscopy or molecular cognition. Furthermore, two pcDNAs containing the influenza HA1 Protein (pcAPCH-Lk1-HA1) and the influenza M2 protein (pcAPCH-Lk1-4M2) respectively were incorporated to the Au@p3k-TransMy nanoparticles, at a ratio of 0.1 mg plasmid per mg nanoparticle, for the purpose of delivery and protein expression. Single-molecule videomicroscopy shows the distribution of the nanoparticles inside the cell and reaching the nucleus.
  C. Au@p3k-TransMy-pcAPCH-Lk1-HA1 nanoparticles incubated in Vero cells we analyzed by immunohistochemistry using a monoclonal antibody against HA1 to show protein expression.
  D. Au@p3k-TransMy-pcAPCH-Lk1-4M2 nanoparticles incubated in Vero cells we analyzed by immunohistochemistry; using a monoclonal antibody against M2 to show protein expression.
  E. pcAPCH-Lk1-HA1 (7345PB) map (SEQ ID NO: 13).
  F. pcAPCH-Lk1-4M2 (6600PB) map (SEQ ID NO: 14).

EXAMPLES

Example 1

Delivery of the Protein Rhodamine by its Binding to Carrier Peptide Sequences which Bind to Cytoplasmic Motor Dynein in Vero Cells 1.1. Materials
1.1.1 Cell Lines and Culture Media Used.

Throughout this example the Vero cell line has been used as a model. Tests of peptides were developed in this established cell line, aneuploid and of indefinite growth in culture. It is derived from the adult African green monkey kidney (Cercopithecus) and it was obtained through the European Collection of Cell Cultures (ECACC), deposited with number 84113001. Their morphology is of fibroblast type and was cultured using Eagle medium modified by Dulbecco (DMEM, Lonza), supplemented with 5% foetal bovine serum (FBS, Lonza) inactivated during 30 minutes at 56° C., 4 mM glutamine (Invitrogen), 200 IU/ml of penicillin and 100 mM streptomycin (Invitrogen). The culture conditions of the cells were 37° C. and an atmosphere of 5% $CO_2$. Routinely, these cells were subcultured 1:6 two times a week, in Easy-T-Flasks culture flasks, 75 $cm^2$ coated with Nunclon® (Nunc). The DMEM culture medium was supplemented in several forms depending on the particular test requirements. Thus, we refer to DMEM SC when it was used without antibiotics, glutamine or FBS. We refer to 2% DMEM when the percentage of SBF is added in this percentage maintaining the other additives in the concentrations mentioned.

1.1.2. Fungible Material Used.

1 ml capacity cryotubes (Nalgene) to maintain the Vero cell line in liquid nitrogen.

Micropipettes (Gilson) with maximum capacities of 1000, 200 and 20 μl.

Micropipette tips (Arc) with filter and free from RNases, to avoid possible contaminations, of 1000, 200 and 20 μl capacity.

1.5 ml capacity tubes (Eppendorf) free from RNAses.

Multi-well cell culture plates of 4, 6, 12 and 24 wells (Nunc).

Coverslip of 12 mm diameter and Conventional rectangular slides (Geber Labs).

1.1.3. Antibodies and Chromogens Used.

anti-DLC8 polyclonal antibody obtained in rabbits immunized with the DLC8 protein bound to 10 Histidine residues expressed in *E. coli* and later purified was used at a 1:50 dilution. Generated in our laboratory.

anti-α tubulin monoclonal antibody (1:2000, Sigma).

Wheat germ agglutinin (WGA) conjugated to the Alexa 488 fluorochrome (1:200, Invitrogen)

Mouse anti IgG antibody conjugated to the Alexa 594 fluorochrome and Mouse anti IgG antibody conjugated to the Alexa 488 fluorochrome (1:200 and 1:300 respectively, Molecular Probes).

Mouse anti IgG antibody conjugated to HRP peroxidase and Rabbit anti IgG antibody conjugated to HRP peroxidase (both 1:5000-10.000, GE Healthcare).

1.1.4 Plasmids.

A vector encoding EGFP-Lamin B1 was a generous gift of Howard Worman from Columbia University New York. A vector encoding enhanced green fluorescent protein (EGFP)-LBR (Lamin B receptor) was kindly provided by Loren Fong from UCLA. EGFP-tubulin and -actin were from Clontech. A vector encoding B23 nucleolar protein was kindly provided by Carmen Rivas Centro nacional de Biotecnologia, Madrid.

1.1.5. Other Reagents.

Triton X-100, Tween 20, bovine serum albumin (BSA), Phosphate buffered saline (PBS) B-mercaptoethanol, SDS, Tris base (Sigma)

RNAse-free water and RNAseZAP solution (Ambion) to eliminate RNAse activity from the working surfaces and materials.

ProLong, mounting reagent to conserve the fluorescence (Invitrogen).

1.1.6. Peptides Used.

A peptide containing the DLC8 binding motif previously described in the African swine fever virus p54 protein (DynPro), Rabies virus P protein (TransRb) and Myosin Va (TransMy) were used and other peptides with irrelevant random aminoacid sequences with an arginine tail as negative controls (INTCT3 peptide) (FIG. 1A). Those peptides were linked to protein Rhodamine B (C- or N-terminus) or tetramethyl-rhodamine (TAMRA) in a lateral chain of aminoacid lysine, as it is described in Table 1.

All the designed peptides used throughout the present example were synthesized by Genecust. The purification thereof was carried out by HPLC obtaining in all cases a degree of purity over 95%. Once synthesized and purified, the peptides were received in the laboratory as a lyophilizate.

Methods 1.2.1 Handling of the Peptides.

According to their molecular weight, the peptides were resuspended in the volume of $H_2O$ with a corresponding degree of purity mQ and sterile, to obtain a stock solution at a concentration of 5 mM. Special attention was paid to avoid turbidity in the solution and tips were always used with a filter to avoid possible cross contaminations. 20 µl aliquots were made and they were conserved at −80° C. until the time of use. To use them their defrosting was slow, in ice.

Peptides working solutions were made from stock solutions in DMEM SC medium (1% PS, 1% G, without FBS) in the 0-100 µM range of concentrations, always in sterile conditions and just before their addition to the cell culture to avoid their degradation.

1.2.2 Incubation of the Peptides in Cell Culture.

$9 \times 10^4$ Vero cells were cultured in 24-well plates the night before the experiment. The next morning, the cells were washed in DMEM SC and the existing medium was replaced by 300 µl of the solutions containing the different peptides in different concentrations. The incubation of the cells with the peptides took place during different time periods ranging from 1 min to 2 hours at 37° C. and 5% $CO_2$ (FIG. 1).

1.2.3. Cytotoxicity Analysis. Cell Viability and Proliferation Assays.

To evaluate cell viability Vero cells seeded in 24 well plates were incubated in DMEM containing delivery peptides DynPro, etc. or negative control INTCT3 linked to Rhodamine B or TAMRA, at concentrations ranging from 0 to 100 µM (FIG. 5b-c). After incubation with peptides for 24 h, cells were harvested and the number of viable cells present in the cell suspensions was determined by Tripan blue (Sigma) dye exclusion assay. Briefly, 20 µl of PBS with Tripan Blue 0.08% were added to equal volume of cell suspension and mixed. After 2 minutes blue cells (dead cells) were counted using a hematocytometer and a conventional light microscope (FIG. 5 b-c).

To evaluate cell proliferation $3 \times 10^4$ Vero cells seeded in 96 well plates were incubated in 50 µl DMEM containing delivery peptides DynPro, etc. or negative control INTCT3 at concentrations ranging from 0 to 100 µM. After 36 h incubation, cell proliferation was determined using CELL-TITER 96 AQUEOUS (Promega) assay, following manufacturer's indications (FIG. 5d-e).

1.2.4. Immunofluorescence.

The cells previously exposed to the peptides were washed with PBS before being fixed with a 3.8% PBS-paraformaldehyde solution at room temperature (RT) for 10 min. After washing with PBS, cells were permeabilized using 0.1% PBS-Triton X-100 for 10 min at RT. After washing with PBS, cells were incubated in blocking solution (2% PBS-bovine serum albumin) at 37° C. for 45 min. Primary antibodies at corresponding dilutions were incubated for 1 h at 37° C. After washing in PBS, cells were incubated for 30 min at RT with secondary antibody at desired concentrations for 45 min at room temperature. Coverslips were mounted with Prolong and observed in a confocal microscope (Leica; FIG. 2). Microtubules were detected by staining with anti-α-tubulin monoclonal antibody (Sigma) diluted 1:1,000. A specific rabbit serum against DLC8 was raised after immunization with nonlabeled DLC8 produced in *E. coli*, as described in Materials. This serum was diluted 1:100 in PBS to detect the DLC8 cellular distribution. Anti-mouse IgG or anti-rabbit IgG Alexa 594-conjugated antibodies (Molecular Probes), diluted 1:200 in PBS, were used as secondary antibodies. Cell-cell contacts and cell membranes were labeled with Wheat germ agglutinin (WGA) conjugated to the Alexa 488 fluorochrome diluted 1:200 in PBS (FIG. 2).

1.2.5. Transfections.

Transfections were performed by using the TransIT 2020 Transfection Reagent from Mirus according to the manufacturer's recommendations. Briefly, Vero cells were grown on 35 mm tissue culture plates, in DMEM 5% serum (1% PS, 1% G), until 80% confluence. Separately, 50 µL of DMEM, serum- and antibiotics-free, was mixed with 0.5 µg of DNA of each plasmid and 1.5 uL of TransIT 2020. The mixture was incubated for 20 min at room temperature before addition to cells. To minimize cytotoxicity and increase the efficiency of the transfection, cells medium was replaced by 300 µl of fresh DMEM 5% serum and antibiotics-free before adding the DNA-TransIT mixture. Similarly, after 4 h, the transfection mixture was removed from cells and 500 μl of fresh medium 5% serum (1% PS, 1% G) was added. At 24 h after transfection, cells were incubated with peptides as explained above and analyzed by confocal microscopy.

1.2.6. Inhibitor Drugs.

Inhibitors of microtubule polymerization were used to demonstrate that movement of the delivery peptide was the expected microtubule motor dependent movement (FIG. 3A). Vero cells at 100% of confluence were incubated in a 35 mm plaque with DynPro at 10 μM (in 500 μL DMEM FBS) for 30 min in a confocal microscope at 37° C. and 5% $CO_2$ and intra and intercellular delivery movement was recorded. Then, 2.5 μM Nocodazole was added to the media and further incubated at 37° C. and 5% $CO_2$ and microtubule associated movement was recorded. After 30-15 min approximately the effect of the drug was noticeable in the cells and movement stopped. After 2.5 h the medium was replaced by fresh medium and recorded in the microscope for 1 h and movement recovery was recorded (FIG. 3A).

Inhibitors of actin polymerization as LatrunculinA were used to test their impact in movement (FIG. 3B). Untransfected or actin transfected Vero cells at 100% of confluence were incubated in a MW4 with Peptide DynProp at 50 μM (in 500 μL DMEM FBS−) for 30 min at 37° C. and 5% $CO_2$. Then, Latrunculin A (0.1 μM) or PBS in controls were added and incubated for 1.5 h at 37° C. and 5% $CO_2$. After washing in PBS, cells were mounted in ProLong Gold antifade reagent.

1.2.7. Time Lapse Video Microscopy.

Confocal microscopy was carried out using a Leica TCS SPE confocal microscope that included an incubation chamber, a CO2 controller and a heating unit. For in vivo observation of movement, selected stacks were recorded every 10 seconds using the Leica Microsystems LAS AF program and the films were displayed at 1-5 frames per second.

In conclusion, the Example 1 shows that peptide sequences that bind a protein from the cell microtubule motor complex, such as molecular motor dynein, may be efficiently used to design a set of carrier peptides that drive intracellular motion linked to microtubules (Table 1). These molecular motor propelled carrier peptides were able to transport with high efficiency any molecule or drug bound to them. Protein Rhodamine B or tetra-methyl-Rhodamine (TAMRA) were linked to the delivery peptide as a payload and added to Vero cells. Its movement was recorded by time-lapse videomicroscopy and compared to that of Rhodamine linked to control peptides with non-dynein binding aminoacid sequence (INTCT3 Internal control; FIG. 1A b,d). The cellular uptake of Rhodamine B was much more efficient and fluorescent proteins quickly accumulated in the cytoplasm of treated cells when it was linked to dynein binding peptides tested (Dynein propelled) as it can be shown in FIG. 1A a,c, for peptide DinPro and in FIG. 1A e,f, respectively, for peptides TransRB and TransBA. Proteins were distributed near the nucleus in the microtubule organizing center area or dispersed through the cytoplasm (FIG. 1, 2). Neither cellular toxicity nor modifications on cell proliferation were found (FIG. 5b-e).

Moreover, the peptide carriers were able to cross nuclear envelope to get into the nucleus (FIG. 4, 5). We found that the carrier peptides could transport fluorescent proteins across the nuclear envelope and the nuclear lamina, as shown in cells transfected with lamin B1-GFP (FIG. 4). It has been shown that these delivery peptides can accumulate in the nucleolus or move around and exit again as it was demonstrated in cells transfected with a plasmid encoding B23 nucleolar protein (FIG. 5a).

Rhodamine B or TAMRA protein linked to delivery peptides were actively transported through cell-cell junctions and connections by adherent junctions, filopodia and cell processes. This pumping out of the protein resulted in quickly spread between cells (FIG. 1-3).

Delivery peptide transport was shown to be dependent on microtubules as the characteristic dynein dependent movement and was stopped with microtubule depolymerizing drugs as nocodazole and after washing out the drug, the transport was recovered FIG. 3A). Nevertheless, other agents depolymerizing actin cytoskeleton (LatrunculinA) had no impact on this transport as expected because it is unrelated (FIG. 3B).

Example 2

Delivery of the Protein Rhodamine by its Binding to Carrier Peptide Sequences which Bind to Cytoplasmic Motor Dynein in Cells of Diverse Origins Materials and Methods Most materials and methods were equal to the previous example with the following peculiarities:

2.1. Cell Lines and Culture Media Used.

In this example we tested diverse cell lines from different origins for use of the delivery peptides.

a) Cell line HEK 293T/17 (American Tissue Culture Collection ATCC No. CRL-11268) is from human embryonic kidney cells transformed with adenovirus 5 and contains, in addition, the SV40 Large T-antigen. HEK 293 cells and several other human cell lines generated by adenovirus transformation of human embryonic kidney cells have morphology (FIG. 1Ca-b) and many properties of immature neurons, such us the presence of mRNA and gene products typically found in neurons.

This cell line was cultured using Eagle medium modified by Dulbecco (DMEM, Lonza), supplemented with 5% foetal bovine serum (FBS, Lonza) inactivated during 30 minutes at 56° C., 4 mM glutamine (Invitrogen), 200 IU/ml of penicillin and 100 mM streptomycin (Invitrogen). The culture conditions of the cells were 37° C. and an atmosphere of 5% $CO_2$. Routinely, these cells were subcultured 1:6 two times a week, in Easy-T-Flasks culture flasks, 75 cm² coated with Nunclon® (Nunc). The DMEM culture medium was supplemented in several forms depending on the particular test requirements. Thus, we refer to DMEM SC when it was used without antibiotics, glutamine or FBS. We refer to 2% DMEM when the percentage of SBF is added in this percentage maintaining the other additives in the concentrations mentioned.

b) Cell line SK-N-MC Human neuroblastoma cells (ATCC HTB-10) Neurogenic origin and Dopamine beta hydrolase activity. This cell line was cultured using Eagle's Minimum Essential medium with pyruvate. The procedure and composition was similar as the previous cell line (FIG. 1Cc-d).

c) COS-7 cell line African green monkey kidney derived from CV-1, a simian cell line (cercopithecus aethiops), by transformation with an origin-defective mutant of SV-40. Fibroblast morphology. ATCC No. CRL-1651, EC ACC 60. This cell line was cultured as explained for a).

d) MDCK cell line Madin-Darby Canine Kidney Epithelial Cells. Cells of epithelial origin positive for keratins and surrounded by basal lamina ATCC CCL-34. This cell line was cultured as explained for a).

e) HeLa in mortal cell line derived from cervical epidermal cancer cells. Epithelial origin, express keratins. ATCC CCL-2. This cell line was cultured as explained for a).

f) Chinese hamster ovary (CHO) cells. CHO cells do not express the Epidermal growth factor receptor (EGFR). ATCC CCL-61. This cell line was cultured as explained for a), adding 4 mM proline (Invitrogen) in medium.

g) THP1 human macrophages cell line (ATCC TIB-202) were grown in suspension with RPMI-1640 Medium. 24 hour previous to peptide treatment, cells were seeded and 5% phorbol myristate acetate (PMA, Lonza) added.

h) KARPAS-422 human lymphocytes cell line derived from non-Hodgkin lymphoma cells were grown in suspension with RPMI-1640 Medium (ICLC: HTL99023).

i) SF9 insect cell line: SF9 Cells are derived from *Spodoptera frugiperda* (Fall Armyworm) (ATCC CRL-1711).

In conclusion, Example 2 shows that microtubule motor complex dynein-binding peptides are useful for the successful delivery of substances in many different cell types from different tissue origins: fibroblasts, epithelial cells, macrophages, lymphocytes, etc., and from different species (human, monkey, hamster, dog) and both transformed or not. This supports application of the dynein-binding delivery peptides in cells derived from solid tumors (cervical epidermal carcinoma) or hematologic malignancies (non-Hodgkin lymphoma).

Example 3

Delivery of the Antigen M2 of Influenza Virus by its Binding to a Carrier Peptide Sequence (DynProp) which Binds to Cytoplasmic Motor Dynein Material and methods of this example are coincident with Example 1 except for the following points:
3.1 Peptides Used.

A peptide containing the DLC8 binding motif previously described in the ASFV p54 protein was used (DynPro) and linked to M2 peptide from Influenza virus. This is an internal core protein of the influenza virus which has been recently characterized to be responsible of the inflammasome response generation in cells during infection. This peptide is currently included in some new vaccine formulations against influenza, together with hemaglutinin or alone. Other peptides with irrelevant sequences were included as negative controls (INTCT3 peptide). All were linked to protein tetramethyl-Rhodamine (TAMRA) and are described in Table 1.

Source, handling of the peptides, and other methods were the same to those described in Example 1.
3.2. Antibodies.

Anti-M2 influenza antigen antibody obtained from rabbits immunized with the M2 influenza protein bound to 10 Histidine residues expressed in baculovirus and later purified was used at a 1:50 dilution. It was generated in our laboratory Immunofluorescence protocols were the same as explained for Example 1.

In conclusion, Example 3 shows that the delivery peptide fused to M2 influenza antigen showed the same dynamic properties as peptide alone or carrying protein Rhodamine (TAMRA). It has the same extended intracellular distribution and intracellular accumulation properties (FIG. 6a). We were able to detect M2 influenza antigen with a specific antibody colocalizing with the delivery peptide demonstrating that it was carried by the peptide to those cellular locations (FIG. 6b). This demonstrates that the load to be successfully transported can be peptides, proteins and or antigens between others.

Example 4

Delivery of the Antigen M2 of Influenza Virus in Mice In Vivo Bound to the Carrier Peptide Sequence (DynPro)

Material and methods of this example are coincident with Example 1 except for the following points.

30 female mice BALB/c (subgroup AnNHsd) of 6-8 weeks age were inoculated intraperitoneal with a volume of 100 µl of the different formulations as explained below, at day 0, 14 and 28 post-inoculation and were bleed at day 0, 14, 28, 42 and 63 to analyze sera.

We compared the effect of the M2 antigen of Influenza virus alone and/or bound to the delivery peptide or the delivery peptide alone, by inoculating 30 mice in 5 groups and comparing the immune response. Also incomplete Freund's adjuvant was added in those formulations indicated (FIG. 6c-e). Different combinations where tested by intraperitoneal inoculation of 2 µg peptide/mice/doses as indicated below:

GROUP A (6 mice): Delivery peptide DynPro in PBS+Freund's Incomplete Adyuvant
GROUP B (6 mice): M2 Influenza antigen in PBS+Freund's Incomplete Adyuvant
GROUP C (6 mice): M2 Influenza antigen linked to delivery peptide DynPro in PBS+Freund's Incomplete Adyuvant
GROUP D (6 mice): M2 Influenza antigen linked to delivery peptide DynPro in PBS
4.1. Specific Antibody Determination.

M2 influenza-specific IgG response was evaluated by ELISA. Purified M2 peptide (GL Biochem) in 50 mM carbonate/bicarbonate buffer, pH 9.6 was used to coat ELISA microplates (Polysorp, Nunc, Denmark) overnight at 4° C. at a concentration of 500 ng/well.

Plates were washed with PBS-Tween 20 (0.1%, PBST) four times, and incubated for 1 hour at 37° C. under constant agitation, with blocking solution (PBST-2% BSA, 100 ul/well). Two-fold dilutions of serum samples from 1:50 to 1:12,800 in blocking buffer were incubated for 1 hour at 37° C. under agitation. Then, plates were washed again 4 times with PBST, and 100 ul/well of anti-mouse monoclonal antibody IgG-HRP conjugated (GElifesciences, USA), diluted 1:2,000 in blocking solution was added. For substrate reaction, plates were washed four times with PBST, and 100 ul/well of 1 mM 2,2'-Azino-bis(3-ethylbenzothiazoline-6-sulfonic acid) (ABTS, KPL, USA) were added to the plates. Peroxidase reaction was allowed to react for 15 min at room temperature to develop immunocomplexes and plates were read at 405 nm in an ELISA microplate reader (Multiskan EX, Thermo Electron Corp, USA). The cut-off threshold discriminating negative and positive sera was set at 2 times the mean of the OD405 from three negative control sera included in each assay (FIG. 6c-e).

In conclusion, Example 4 shows the mice inoculation with the M2 antigen of influenza alone or bound to the delivery peptide, to compare the immune response elicited. All mice remained healthy, stable in weight and temperature with no signs of toxicity. The sera obtained from the mice were analyzed to assay for an antibody response. The first inoculation showed a strong antibody response in mice inoculated with the M2 influenza antigen with Freund's Incomplete adjuvant and lower initial response in those inoculated with M2 influenza antigen bound to the delivery peptide (FIG. 6c). After a second inoculation, the antibody response rose similarly with or without the delivery peptide being the proof that this method is suitable for vaccination (FIG. 6d-e).

Example 5

Delivery of Nanoparticles Functionalized with the Dynein Transported Peptide Sequence Material and methods of this example are coincident with Example 1 adding the following points:
5.1.1. Chemicals for Nanoparticle Synthesis.

All the chemicals were of reagent grade and were used without further purification. Hydrogen tetrachloroaureate (III) trihydrate (99.9+%), (N-(3-dimethylaminopropyl)-N'-ethylcarbodiimide hydrochloride, and 2-[N-morpholino]ethanesulfonic acid (99.5%) were purchase from Sigma-Aldrich, N-(2-mercaptopropionyl)glycine (>98%) and N-hydroxysulfosuccinimide (>97%) from Fluka, NaBH$_4$ (98%) from Lancaster, ASFV p54 protein-derived peptide sequences (M2-DynPro, DynPro and the control peptide INTCT3) from Genecust, $CH_3O$-PEG-$NH_2$ (750 Da) from Rapp-Polymere. House distilled water was further purified using a Milli-Q reagent grade water system (Millipore). Buffers were prepared according to standard laboratory procedure. Other chemicals were reagent grade and used as received.

Methods 5.2.1 Nanoparticles Synthesis and Characterization.

General Procedures. UV-vis spectra were carried out with Varian Cary 50 spectrophotometer. Florescence spectra were carried out with a LS-55 Fluorescence Spectrometer. Zeta potential (ζ in mV) measurements were done using a Zeta-PALS analyser from Brookhaven. All spectra were collected in 50 mM MES, pH 6.5. For TEM examinations, a single drop (10 μL) of the aqueous solution (0.1 mg·mL$^{-1}$) of the gold nanoparticles was placed onto a copper grid coated with a carbon film. The grid was left to dry in air for several hours at room temperature. TEM analysis was carried out on a Tecnai 20 FEI microscope operated at 200 KV. Particle size distribution of the Au nanoparticles was evaluated from several micrographs using a program for image processing and analysis (ImageJ). The number of particles selected for consideration was around 400, which resulted in a stable size-distribution statistic.

Au@tiopronin production: Hydrogen tetrachloroaureate (III) trihydrate (0.15 g, 0.4 mmol, 1 equiv) and N-(2-mercaptopropionyl)glycine (tiopronin; 0.19 g, 1.2 mmol, 3 equiv) were codissolved in 20 mL of 6:1 methanol/acetic acid, giving a ruby red solution. $NaBH_4$ (0.30 g, 8.0 mmol, 20 equiv) in 7.5 mL of $H_2O$ was added with rapid stirring. The black suspension that was formed was stirred for an additional 30 min after cooling, and the solvent was then removed under vacuum at 40° C. The crude Au@tiopronin was completely insoluble in methanol but quite soluble in water. It was purified by dialysis, in which the pH of 130 mg of crude product dissolved in 20 mL of water was adjusted to 1 by dropwise addition of concentrated HCl. This solution was loaded into 15 cm segments of seamless cellulose ester dialysis membrane (Sigma, MWCO 10 kDa), placed in 4 L beakers of water, and stirred slowly, recharging with fresh water approximately every 10 h over the course of 72 h. The dark blue Au@tiopronin solutions were collected from the dialysis tubes and were lyophilized. Yield: 96 mg. Average diameter: 2.8 nm. UV/vis (H2O) υ=450, 560 nm (surface plasmon band). Z-potential ζ (mV)=−28.00.

Peptide binding to nanoparticles (Au@#peptide#): (N-(3-Dimethylaminopropyl)-N'-ethylcarbodiimide hydrochloride (EDC; 2 mg, 0.01 mmol) and N-hydroxysulfosuccinimide (sulfo NHS; 3 mg, 0.014 mmol) were added to 4 mL of Au@tiopronin (2 mg) in 2-[N-morpholino]ethanesulfonic acid (MES) (50 mM, pH 6.5). The peptide DynPro TAMRA (0.138 μmol) or peptide M2-DynPro TAMRA (0.130 μmol) or peptide INTCT3 TAMRA (0.138 μmol) or TAMRA (0.036 μmol) were added and the mixture was stirred overnight. Then, this solution was loaded into centrifugal filters (Amicon Ultra-0.5 mL) for purification of uncoupled peptide DynPro or TAMRA and excess of EDC/sulfo NHS. UV/vis ($H_2O$) υ=450, 560 nm (surface plasmon band). Z-potential ζ (DynProTAMRA)=−14.95±7.85 mV; ζ (M2-DynProTAMRA)=−18.62±4.01 mV and (INTCT3TAMRA)=−36.32±3.98 mV; ζ (TAMRA)=−3.46±1.96 mV; Scheme of nanoparticle structure (FIG. 7*a*).

Au@tiopronin nanoparticles preparation: Au@tiopronin nanoparticles were prepared using the procedure of Murray et al. (Templeton). The reaction was executed in a methanolic/acetic acid mixture. Codissolution of $HAuCl_4$ and tiopronin gave a stable ruby-red solution. The addition of $NaBH_4$ reductant provided a dark brown solution. The functionalization of nanoparticles with the #peptide# and $CH_3O$-PEG-$NH_2$ was carried out using the following procedure. The suspension was shaken for about 30 min, and then the solvent was removed. The nanoparticles were purified by dialysis and characterized UV/vis and TEM. A mean diameter of 2.8 nm was found for the gold core of the nanoparticles. The UV/vis absorption spectrum showed a nondetectable surface plasmon band (SP band) as consequence of the small size of the clusters. Fluorescence and MS spectra confirmed the presence of TAMRA labeled peptide on the nanoparticles. The functionalization of Au@tiopronin with the peptide sequence (DynPro) was carried out using the reactivity of the free carboxyl group of the tiopronin (Scheme FIG. 7*a*). The reaction utilizes the water-soluble carbodiimide EDC to catalyze reactions between the nanoparticle acid groups and any of the amine groups of the peptide. We included sulfo NHS in the reaction mixture to improve the efficiency of the carbodiimidemediated amide-forming reaction by producing hydrolysis-resistant active ester reaction intermediates. The resultant nanoparticles were analyzed by UV/vis, Fluorescence and mass spectroscopy (MS), as well as Zeta potential analysis and TEM; non-aggregation was observed after peptide coupling.

5.2.2 Incubation of the Nanoparticles in Cells

All the experiments were carried out under sterile and safe conditions working with microbiological class II safety cabinets. The nanoparticles were resuspended in H2O, with a degree of purity mQ and sterile, to obtain stock solutions at different concentrations. Special attention was paid to avoid turbidity in the solution and tips were always used with a filter to avoid possible cross contaminations. 500 μl aliquots were stored at 4° C. until the time of use. Working solutions of the nanoparticles were made from stock solutions in DMEM SC medium (1% PS, 1% G) and adjusted to 8 μM, which was the optimal concentration. This procedure was performed just before the nanoparticles were added to the cell culture to avoid degradation. In order to perform in vivo assays, 106 Vero cells were cultured in 35 mm glass plates overnight. The cells were washed in DMEM SC (1% PS, 1% G) and the existing medium was replaced by 300 ml of the solutions containing the nanoparticles at optimal concentration. The nanoparticles were incubated in incubation chambers at 37° C. and 5% CO2 at 8 mM and observed with the confocal microscope. The incubation time periods ranged from 1 minute to 3 hours to observe different stages of accumulation in the cells.

5.3.1 Cytotoxicity Analysis. Cell Viability and Proliferation Assays.

To evaluate cell viability Vero cells seeded in 24 well plates were incubated in DMEM containing Au-tiopronin nanoparticles functionalized with delivery peptides DynPro, DynPro-M2 or negative control INTCT3 bound to nanoparticles at concentrations ranging from 0 to 50 µM. After incubation with peptides for 24 h, cells were harvested and the number of viable cells present in the cell suspensions was determined by Tripan blue (Sigma) dye exclusion assay (FIG. 7d). Briefly, 20 µl of PBS with Tripan Blue 0.08% were added to equal volume of cell suspension and mixed. After 2 minutes blue cells (dead cells) were counted using a hematocytometer and a conventional light microscope.

To evaluate cell proliferation $3\times10^4$ Vero cells seeded in 96 well plates were incubated in 50 µl DMEM containing delivery peptides DynPro or negative control INTCT3 bound to nanoparticles at concentrations ranging from 0 to 50 µM. After 36 h incubation, cell proliferation was determined using CELLTITER 96 AQUEOUS (Promega) assay, following manufacturer's indications (FIG. 7e).

In conclusion Example 5 shows that delivery dynein-binding peptide can be bound to different drugs and chemicals both organic (protein rhodamine) or inorganic (metal Au) to form nanoparticles functionalized with the delivery peptides. These nanoparticles do not show any toxicity or proliferative effect in cells. This nanoparticles can be further be bound to drugs or pharmaceuticals (such as tiopronin used in renal diseases) to other peptides or antigens, such as M2 influenza peptide) and others as the state of the art indicates. They retain distribution, intracellular accumulation and intercellular diffusion abilities of the delivery dynein-binding peptides and their ability to enter across nuclear membrane or from one cell to another irrespective of their size.

Example 6

Antiviral Effect of Peptide Fused to Nanoparticles

Nanoparticles stabilize peptides to be administered for antiviral treatments and improve biodisponibility and other pharmacological properties of the peptides to be used for antiviral treatments in vivo. In this example, we demonstrate the antiviral effect of peptide DynPro and control INTCT3 fused to gold-tiopronin-nanoparticles of Example 5.

Material and methods of this example are coincident with Example 1 adding the following points:

6.1.1. Viral Isolates Used.

The isolate of the African swine fever virus used in the inhibition tests of the infection was BA71V, adapted to grow in the Vero cell line. The viral stock was conserved in aliquots of 100 µl at −80° C. in DMEM medium supplemented with 15% foetal bovine serum. At the time of their use, the aliquots necessary were quickly defrosted in a bath at 37° C. and kept in ice.

6.1.2. Antibodies and Chromogens Used.

anti-p30 monoclonal antibody: developed in the laboratory of Dr. Jose Angel Martínez Escribano, specifically recognises and detects early protein p30 of the ASFV.

anti-p72 monoclonal antibody (anti-p73): marketed by Ingenasa, specifically recognises and detects structural late protein mainly p72 or p73 of the ASFV.

Mouse anti IgG antibody conjugated to the Alexa 594 fluorochrome (Molecular Probes).

Mouse anti IgG antibody conjugated to the Alexa 488 fluorochrome (Molecular Probes).

Mouse anti IgG antibody conjugated to HRP peroxidase (GE Healthcare).

Rabbit anti IgG antibody conjugated to HRP peroxidase (GE Healthcare).

6.2.1 Antiviral Effect of Peptide Bound to Nanoparticles.

$9\times10^4$ Vero cells were cultured in 24-well plates the night before the experiment. The next morning, the cells were washed in DMEM SC and the existing medium was replaced by 300 µl of the solutions containing the different peptides bound to nanoparticles at different concentrations. The incubation of the cells with the peptides bound to nanoparticles took place during 1 hour at 37° C. and 5% $CO_2$, after which the cells were infected with the ASFV. To infect the cells, the existing cell culture was removed and it was replaced to 2% 350 µl/well containing the corresponding quantity to obtain an infection multiplicity of 1 plaque forming unit (pfu) per cell. The infection was allowed to run until the desired time at 37° C. and 5% $CO_2$.

After the absorption period (2 h at 37° C.) the residual virus was eliminated by washing twice with DMEM SC and finally the cells were left in 300 µl of fresh DMEM SC containing the corresponding concentration of peptides. The infection was allowed to run at 37° C. for the desired time in each experiment, depending on the parameter of the infection to be analysed.

6.2.2 Detection of Cells Infected by ASFV by Indirect Immunofluorescence (IIF).

The detection of cells infected by ASFV in cells previously exposed to the peptides bound to nanoparticles was performed 6 hours post-infection. The IIF techniques used to detect those cells infected by ASFV by immunofluorescence were conventional. In summary, the cells were washed with 1 ml of PBS before being fixed with a 3.8% PBS-paraformaldehyde solution at ambient temperature during 10 minutes. The residual paraformaldehyde was then eliminated by washing the cells 3 times with 1 ml of PBS. The permeabilization of cell membranes was performed using 0.2% PBS-Triton X-100 during 15 minutes at room temperature. After another 3 washes with PBS, the cells were incubated at 37° C. in blocking solution (3% PBS-BSA) during 45 minutes. As viral antigen to detect, the early protein of ASFV p30 [5] was chosen and its detection was carried out using the anti-p30 antibody diluted in PBS 1:200 during 1 hour at 37° C. The cells were washed 3 times with PBS and they were incubated for 30 minutes at ambient temperature with a solution with mouse anti-IgG antibody diluted 1:300 in PBS. The cells were washed in PBS and finally a marking of nuclei with Hoechst 3332 was incorporated. Finally, the coverslips containing the cells were mounted on slides using Prolong as mounting medium. The preparations were observed in a conventional fluorescence microscope (Leica) to count the number of positive cells for the viral antigen p30.

6.2.3 Evaluation of Antiviral Effect of Peptide Bound Nanoparticles by Analysis of the Synthesis of ASF Viral Proteins by Western Blot.

The viral proteins subject to analysis were early ASFV p30 protein expressed during the initial phases of the infection and the p72 protein (also called p73) expressed during the late phase of the infection. The western blot was carried out on the cells, which were washed with 1 ml of cold PBS, before being collected in 50 µl of frozen RIPA protein extraction buffer (150 mM NaCl, 5 mM β-mercaptoetanol, 1% NP40, 1% SDS and 50 mM Tris-HCl pH=8). They were incubated at 4° C. with orbital stirring during 20 minutes to solubilize the proteins and then they were centrifuged at 12,000 rpm in a table centrifuge at 4° C. during 10 minutes. The precipitates were discarded and the supernatants were collected, which were stored at −70° C. until their analysis by western blot.

The samples were defrosted in ice and the quantity of protein in the different samples was quantified by the Bradford method. 20 µg of total denaturised protein at 100° C. during 5 minutes were separated by electrophoresis in 15% acrylamide:bis-acrylamide gels during 90 minutes at 100 V constant. The separated proteins were transferred to a nitrocellulose membrane during 90 minutes at 100 V constant in the presence of a transfer buffer (Tris-Glycine, 20% Methanol). The membrane was blocked in the presence of 50 ml of 5% skimmed PBS-milk powder at room temperature during a minimum of 1 hour with orbital stirring. Then, the membrane was hybridized with 10 ml of the anti-DLC8 polyclonal antibody diluted 1:50 in PBS during 1 hour at room temperature with stirring. After this time, the membrane was washed 3 times with 20 ml of 0.05% PBS-Tween at room temperature during 15 minutes each. Incubation with the secondary rabbit anti-IgG antibody conjugated to peroxidase and diluted 1:4000 in PBS lasted 1 h at room temperature with stirring. Then, the membranes were washed three times with 0.005% PBS-Tween during 15 minutes each. Finally, the detection by chemoluminescence using ECL was performed following the manufacturer's instructions in conventional manner.

As starting sample to analyse, total soluble protein extracts were used from Vero cells exposed or not to the different peptide bound nanoparticles and later infected or not with ASFV during 16 hours.

As primary antibodies the anti-p30 monoclonal antibody diluted 1:100 in PBS and the anti-p72 monoclonal antibody diluted 1:2000 in PBS were used in independent membranes. The membranes were incubated with both antibodies for 1 hour at room temperature with orbital stirring. As secondary antibody, the mouse anti-IgG antibody conjugated to peroxidase were used in both cases. Finally, the densitometry of the chemoluminescence reaction for quantifying and relativizing the quantity of protein existing in each band detected.

In conclusion, Example 6 shows that nanoparticles functionalized to delivery peptide are useful as antiviral agents and its pharmacological properties as prolonged half-life make them especially suitable for any pharmaceutical composition.

Example 7

Construction of New Pegylated Molecular Motor Powered Au-Tiopronin Nanoparticles to Increase Nanoparticle Stability Properties and In Vivo Half-Life Materials and Methods are coincident with precedent Example 5 with the following specific changes in nanoparticle synthesis and preparation:

7.1. Pegylated Nanoparticles Synthesis and Characterization.

Au@peptide/PEG preparation: (N-(3-Dimethylaminopropyl)-N'-ethylcarbodiimide hydrochloride (EDC; 2 mg, 0.01 mmol) and N-hydroxysulfosuccinimide (sulfo NHS; 3 mg, 0.014 mmol) were added to 4 mL of Au@tiopronin (2 mg) in 2-[N-morpholino]ethanesulfonic acid (MES) (50 mM, pH 6.5). Then, the peptide DynPro (0.138 μmol) or peptide M2-DynPro (0.130 μmol) or peptide INTCT3 (0.138 μmol) or TAMRA (0.036 μmol) were added and stirred for 20 minutes; after this time for coupling the peptide to the nanoparticles, $CH_3O$-PEG-$NH_2$ (0.525 mg, 700 nmol) was added to the solutions and left overnight under stirring. The different preparations were loaded into centrifugal filters (Amicon Ultra-0.5 mL) for purification of uncoupled peptides or TAMRA, $CH_3O$-PEG-$NH_2$ and excess of EDC/sulfo NHS. UV/vis ($H_2O$) u=450, 560 nm (surface plasmon band). Z-potential ζ (DynProTAMRA/PEG)=−1.60±1.21 mV; ζ (M2-DynProTAMRA/PEG)=−18.13±5.85 mV; and ζ (INTCT3TAMRA/PEG)=−30.33±5.53 mV; ζ (TAMRA/PEG)=−0.03±0.03 mV. Nanoparticle composition scheme (FIG. 7*a*).

Addition on cell culture and evaluation was performed as in Example 5.

In conclusion, Example 7 shows that nanoparticles functionalized with the delivery peptide can be bound to different loads such as polymers, being polyethylene glycol (PEG) polymer chains, a characteristic example with many applications in pharmaceutics and medicine. These nanoparticles retain distribution, intracellular accumulation and intercellular diffusion abilities of the delivery dynein binding peptides and their ability to enter across nuclear membrane or from one cell to another irrespective of their size.

Example 8

Construction of New Molecular Motor Powered Au-Tiopronin-Carbohydrates Nanoparticles to Deliver hTERT or CEA Peptide for Diagnosis, Therapy or Anticancer Vaccination Materials and Methods are coincident with precedent Example 5 with the following specific changes in nanoparticle synthesis and preparation:

Sequences of hTERT and/or CEA peptide were bound to Au-Tiopronin nanoparticles functionalized with the dynein-binding peptide DynPro. Addition on cell culture and evaluation was the same as in Example 5 but in addition this formulation was tested in cell lines from tumor origin. Several cell lines derived from the most common human tumors were studied, including HeLa cells (from cervical carcinoma carrying human papilloma virus, with wt but inactivated p53), Cell line SK-N-MC Human neuroblastoma cells, CARPAS 446 human lymphocytes cell lines derived from non-Hodgkin lymphoma cells, A431 cells (epidermoid carcinoma; mutated p53), HT29 cells (colon adenocarcinoma; mutated p53), MCF7 cells (breast adenocarcinoma; wt p53), Saos-2 cells (osteosarcoma; absence of p53), and three uveal melanoma cell lines: MKTBr (mutated p53), OCM1 (mutated p53), and Sp6 (wt p53).

Cell viability was evaluated after nanoparticle treatment. A total of $4\times10^4$ cells/well were plated in 24-multiwell culture plates; Cell density was evaluated by the crystal violet method. Briefly, cells were fixed with 1% glutaraldehyde for 10 minutes, washed twice in PBS, and stained with 1.5 mL of 0.1% crystal violet solution for 30 minutes. Wells were rinsed in a beaker with a slow stream of distilled water until the dye was washed off and left to dry overnight. Absorbance was read at 590 nm by dye uptake in 10% acetic acid.

In conclusion Example 8 shows that nanoparticles functionalized with delivery peptide carrying tumor peptides (CEA, hTERT) are useful as a delivery system for tumor cells with potential use in diagnosis and anti-cancer vaccination.

Example 9

Construction of Molecular Motor Powered Au-Tiopronin Nanoparticles Carrying an Antitumoral hTERT Inhibitor Peptide Materials and Methods are coincident with precedent Example 5 with the following specific changes in nanoparticle synthesis and preparation:

Addition on cell culture and evaluation was the same as in Example 5 but in addition, this formulation was tested in cell lines from tumor origin. Several cell lines derived from the most common human tumors were studied, including HeLa cells (from cervical carcinoma carrying human papilloma virus, with wt but inactivated p53), A431 cells (epidermoid carcinoma; mutated p53), HT29 cells (colon adenocarcinoma; mutated p53), MCF7 cells (breast adenocarcinoma; wt p53), Cell line SK-N-MC Human neuroblastoma cells, CARPAS 446 human lymphocytes cell line derived from non-Hodgkin lymphoma cells and Saos-2 cells (osteosarcoma; absence of p53).

Cell viability was evaluated after nanoparticle treatment. A total of $4\times10^4$ cells/well were plated in 24-multiwell culture plates; Cell density was evaluated by the crystal violet method. Briefly, cells were fixed with 1% glutaraldehyde for 10 minutes, washed twice in PBS, and stained with 1.5 mL of 0.1% crystal violet solution for 30 minutes. Wells were rinsed in a beaker with a slow stream of distilled water until the dye was washed off and left to dry overnight. Absorbance was read at 590 nm by dye uptake in 10% acetic acid.

In conclusion, Example 9 shows that nanoparticles functionalized with delivery peptide carrying anti-TERT peptide were cytotoxic in cells of tumor origin being the basis for a new delivery system for cancer therapy agents.

Example 10

Subcellular Distribution of a Peptide Formulation Comprising SEQ ID NO: 11 (TransMy)

Material and methods of this example are coincident with Example 1 excepting for following points:
10.1 Peptide Used:

A peptide with the SEQ ID NO: 11 (TransMy) linked to an octa-arginine tail was used. The peptide INTCT3 was used as control. Both peptides were linked to protein tetramethyl-Rhodamine (TAMRA) and are described in Table 1.

Source, handling of the peptides, and other methods were the same to those described in Example 1.

FIG. 8 shows the efficient intracellular accumulation of the said peptides and their intra and intercellular distribution. It shows their localization throughout the cytosol, and, what is of utmost importance, also in the nucleus.

Example 11

Construction of TransMy Peptide of SEQ ID NO: 11 Functionalized with PEGylated Au-Tiopronin Nanoparticles to Deliver a DNA Vaccine Encoding the antigens HA1 (Haemaglutinin) and M2 of Influenza Virus Materials and Methods are coincident with precedent Example 5 with the following specific changes in nanoparticle synthesis and preparation:

11.1. Pegylated Nanoparticles Synthesis and Characterization: Au@p3k-TransMy

Au@peptide/PEG preparation: (N-(3-Dimethylaminopropyl)-N'-ethylcarbodiimide hydrochloride (EDC; 2 mg, 0.01 mmol) and N-hydroxysulfosuccinimide (sulfo NHS; 3 mg, 0.014 mmol) were added to 4 mL of Au@tiopronin (2 mg) in 2-[N-morpholino]ethanesulfonic acid (MES) (50 mM, pH 6.5). Then, the peptide TransMy (0.138 µmol) or peptide INTCT3 (0.138 µmol) or TAMRA alone (0.036 µmol) were added and stirred for 20 minutes; after this time for coupling the peptide to the nanoparticles, $CH_3O$-PEG-$NH_2$ (0.525 mg, 700 nmol) was added to the solutions and left overnight under stirring. The different preparations were loaded into centrifugal filters (Amicon Ultra-0.5 mL) for purification of uncoupled peptides or TAMRA, $CH_3O$-PEG-$NH_2$ and excess of EDC/sulfo NHS. UV/vis ($H_2O$) $\upsilon$=450, 560 nm (surface plasmon band). Z-potential $\zeta$ (TransMyTAMRA/PEG)=−1.59±1.22 mV; $\zeta$ (INTCT3TAMRA/PEG)=−30.33±5.53 mV; and $\zeta$ (TAMRA/PEG)=−0.03±0.03 mV.

Plasmid incorporation: As an example, a DNA vaccine composition comprising a plasmid pcDNAs encoding for the HA I influenza hemagglutinin (pcAPCH-Lk1-HA1) and/or M2 protein (pcAPCH-Lk1-4M2) expression cassette was incorporated in the Au@p3k-TransMy nanoparticles at a ratio of 0.1 mg plasmid/mg nanoparticle for the purpose of delivery and protein expression. Addition on cell culture and evaluation was performed as shown for Example 5.

Figure 8A:
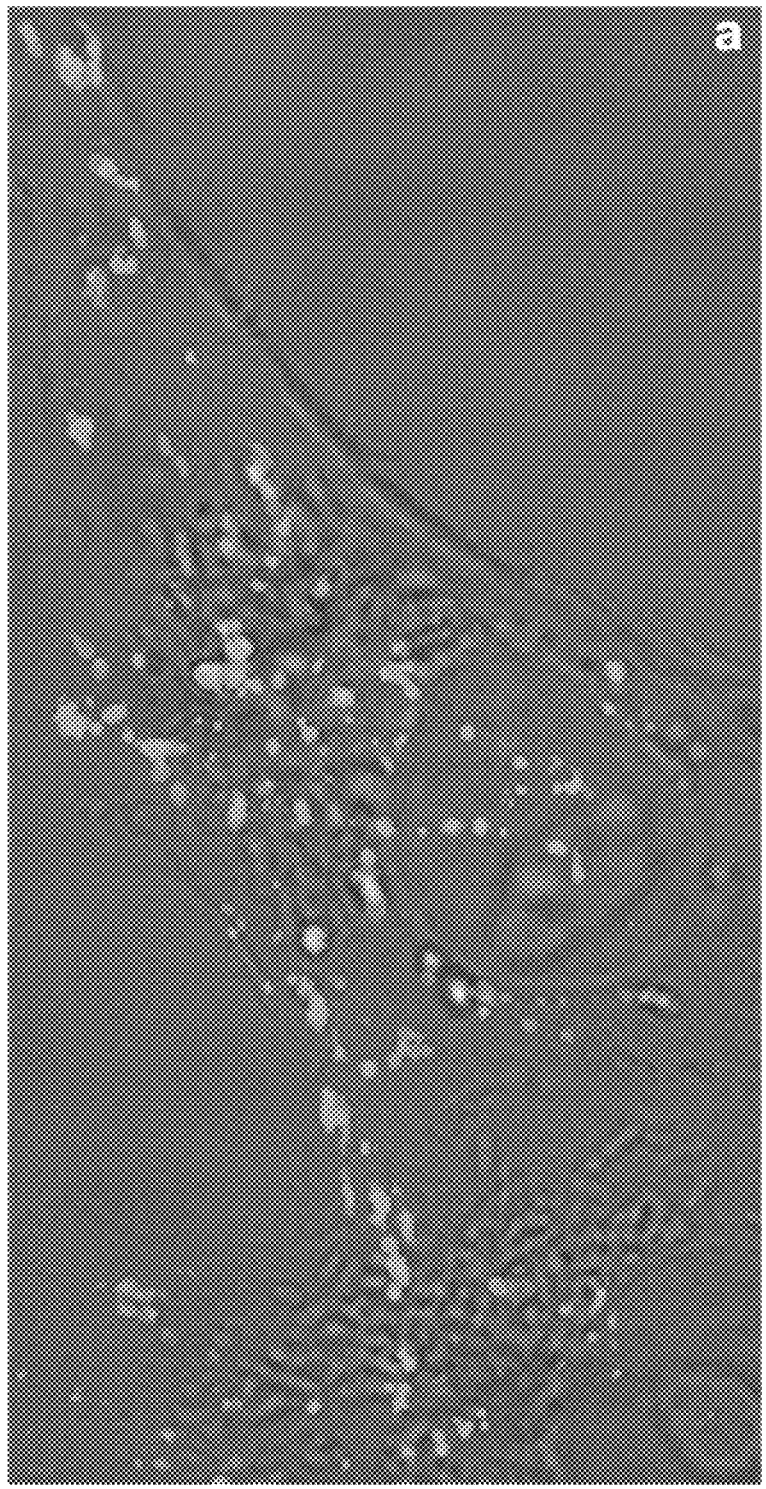
Figure 8B:
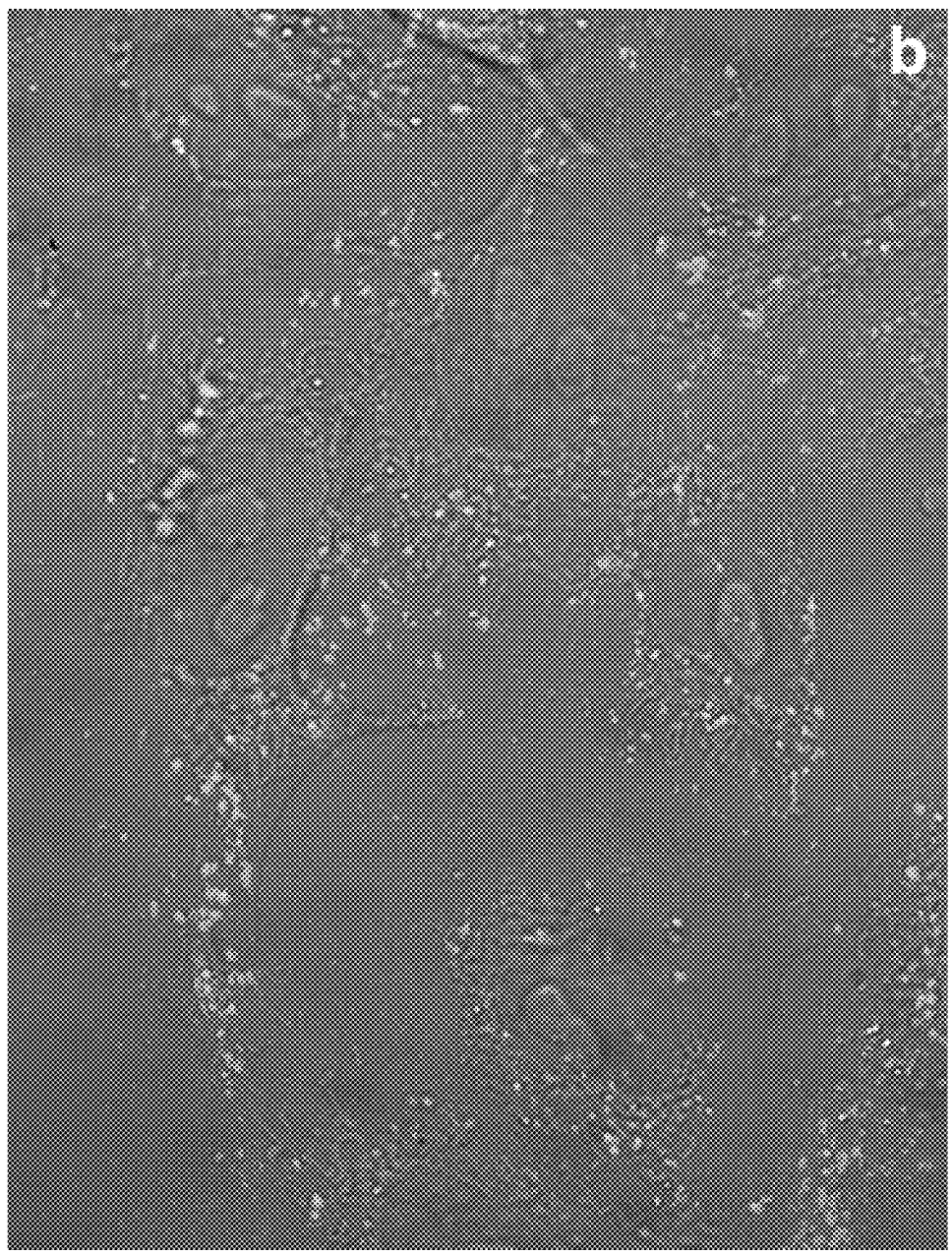
Figure 8C:
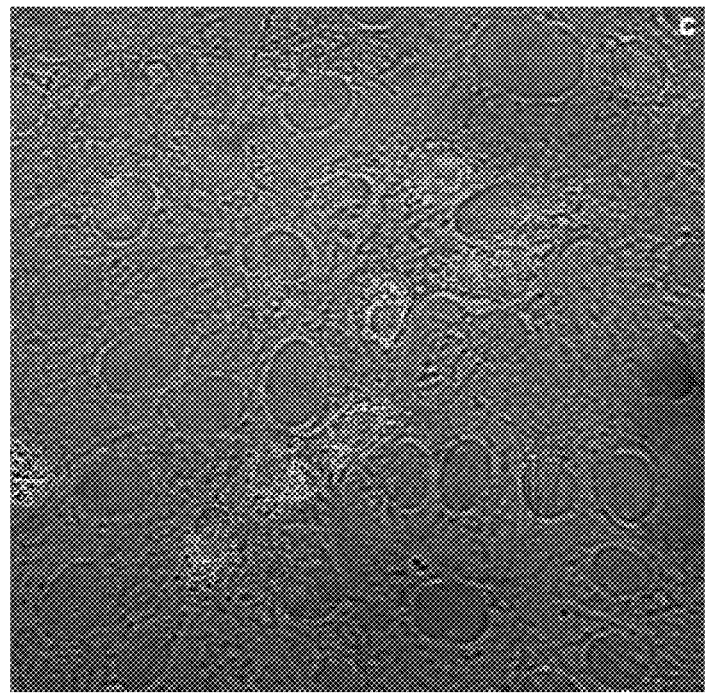
Figure 8D:
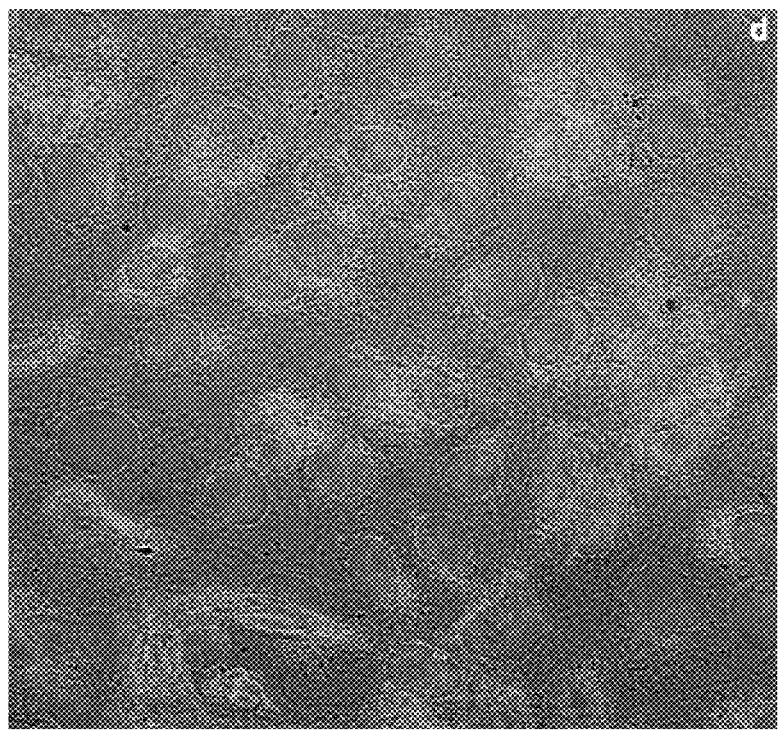

In conclusion, Example 11 shows that nanoparticles functionalized with the delivery peptide can be bound to different loads such as polymers, being polyethylene glycol (PEG) polymer chains, a characteristic example with many applications in pharmaceutics and medicine. These nanoparticles retain distribution, intracellular accumulation and intercellular diffusion abilities of the other formulations of delivery dynein binding peptides and their ability to enter across nuclear membrane or from one cell to another irrespective of their size as it is shown in FIG. 8B.

Figure 8E:
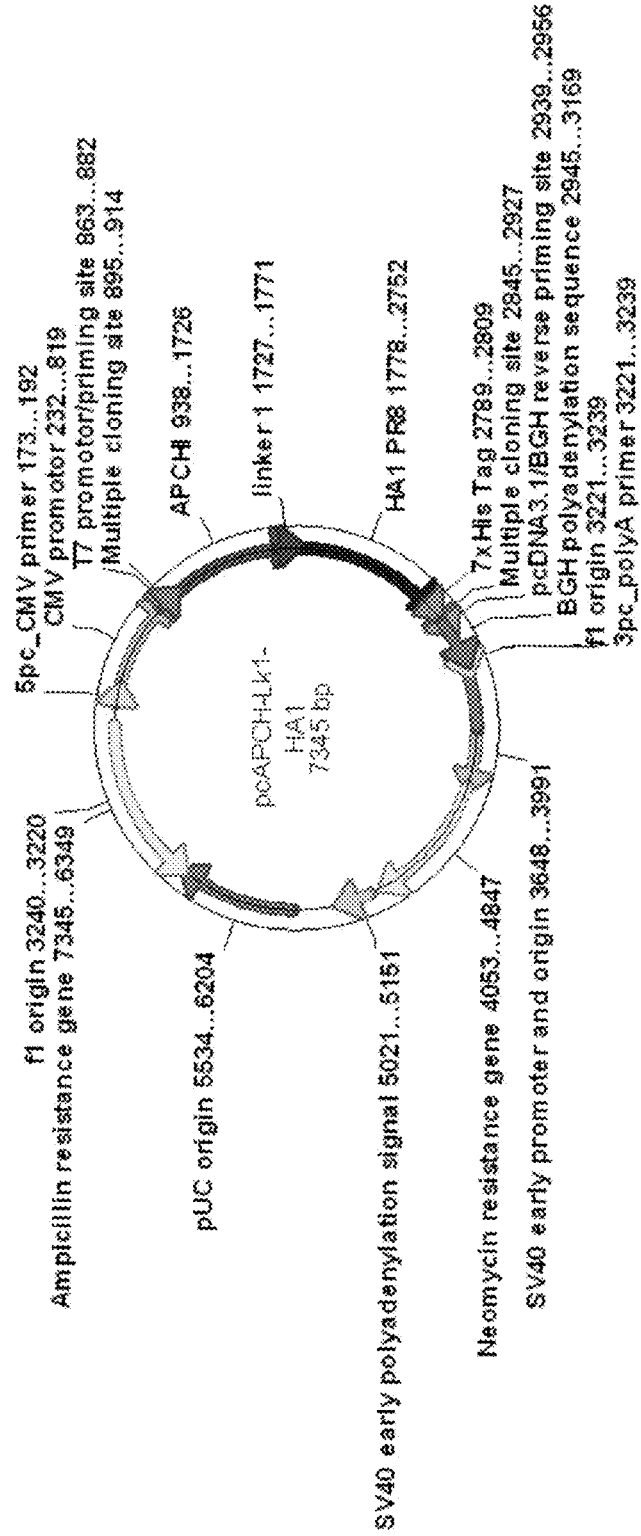
Figure 8F:
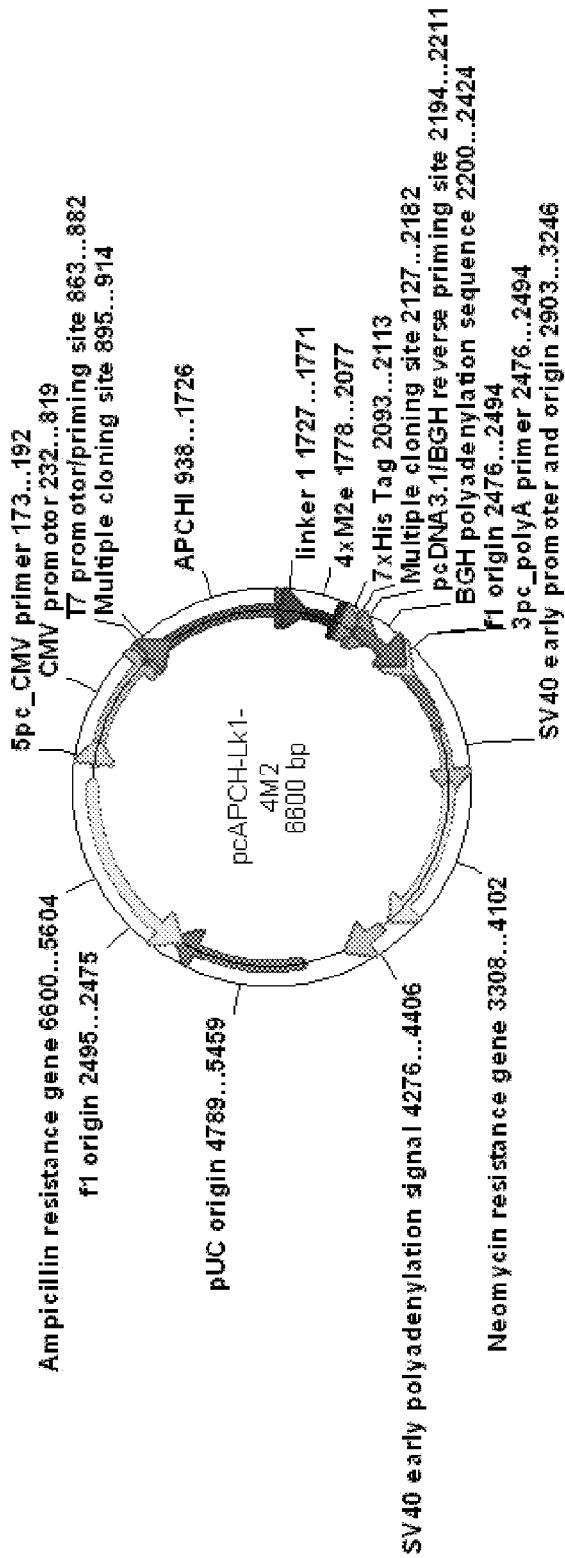

Furthermore, the successful expression of each plasmid vector or DNA vaccine was detected in cells using immunofluorescence with an antibody against influenza haemaglutinin (anti-HA; FIG. 8E) and against influenza M2 (antibody anti-M2; FIG. 8F).

REFERENCES

Bao L, Guo H, Huang X, Tammana S, Wong M, McIvor R S, Zhou X. High-titer lentiviral vectors stimulate fetal calf serum-specific human CD4 T-cell responses: implications in human gene therapy. Gene Ther 16:788-95, 2009

Bareford, L. M. & Swaan, P. W. Endocytic mechanisms for targeted drug delivery. Adv. Drug Deliv. Rev. 59: 748-758, 2007.

Branden L. J., A. J. Mohamed, C. I. E. Smith. A peptide nucleic acid nuclear localization signal fusion that mediates nuclear transport of DNA. Nat. Biotechnol. 17: 784-787, 1999

Ciolina C., G. Byk, F. Blanche, V. Thuillier, D. Scherman, P. Wils, Coupling of nuclear localization signals to plasmid DNA and specific interaction of the conjugates with importin, Bioconjug. Chem. 10 49-55, 1999

Dujardin D. L., L. E. Barnhart, S. A. Stehman, E. R. Gomes, G. G. Gundersen and Richard B. Vallee. A role for cytoplasmic dynein and LIS1 in directed cell movement. The Journal of Cell Biology 163, Number 6: 1205-1211, 2003

Futaki S., Membrane-permeable arginine-rich peptides and the translocation mechanisms, Adv. Drug Deliv. Rev. 57 547-558, 2005

Hambley, T. W. and W. N. Hait. Is anticancer drug development heading in the right direction? Cancer Res. 69:1259-1262, 2009

Howard, M. D., Jay, M., Dziublal, T. D. & Lu, X. L. PEGylation of nanocarrier drug delivery systems: state of the art. *J. Biomed. Nanotechnol.* 4, 133-148, 2008

Ichinohe T, Pang I K, Iwasaki A. Influenza virus activates inflammasomes via its intracellular M2 ion channel. Nat Immunol. 11: 404-10, 2010

Iyer, A. K., G. Khaled, J. Fang, and H. Maeda. Exploiting the enhanced permeability and retention effect for tumor targeting. Drug Discov. Today. 11:812-818, 2006

Liao C, Zhao M J, Zhao J, et al. Overexpression of LPTS-L in hepatocellular carcinoma cell line SMMC-7721 induces crisis. World J Gastroenterol 2002; 8:1050-1052

Melo S. A., C. Moutinho, S. Ropero, G. A. Calin, S. Rossi, R. Spizzo, A. F. Fernandez, V. Davalos, A. Villanueva, G. Montoya, H. Yamamoto, S. Schwartz and M. Esteller. A Genetic Defect in Exportin-5 Traps PrecursorMicroRNAs in the Nucleus of Cancer Cells. Cancer Cell 18, 303-315, 2010.

Moffatt S, Hays J, HogenEsch H, Mittal S K. Circumvention of vector-specific neutralizing antibody response by alternating use of human and non-human adenoviruses: implications in gene therapy. Virology 272: 159-167, 2000

Pante, N. & Kann, M. Nuclear pore complex is able to transport macromolecules with diameters of similar to 39 nm. Mol. Biol. Cell 13, 425-434, 2002.

Rothbard J. B., T. C. Jessop, R. S. Lewis, B. A. Murray, P. A. Wender. Role of membrane potential and hydrogen bonding in the mechanism of translocation of guanidinium-rich peptides into cells, J. Am. Chem. Soc. 126: 9506-9507, 2004

Salina D., K. Bodoor, D. Mark Eckley, T. A. Schroer, J. B. Rattner and B. Burke. Cytoplasmic Dynein as a Facilitator of Nuclear Envelope Breakdown. Cell 108, 97-107, 2002

Sandgren S., F. Cheng, M. Belting, Nuclear targeting of macromolecular polyanions by an HIV-Tat derived peptide. Role for cellsurface proteoglycans. J. Biol. Chem. 277: 38877-38883, 2002

Sebestyen M. G., J. J. Ludtke, M. C. Bassik, G. Zhang, V. Budker, E. A. Lukhtanov, J. E. Hagstrom, J. A. Wolff DNA vector chemistry: the covalent attachment of signal peptides to plasmid DNA, Nat. Biotechol. 16: 80-85, 1998

Subramanian A., P. Ranganathan, S. L. Diamond, Nuclear targeting peptide scaffolds for lipofection of nondividing mammalian cells, Nat. Biotechnol. 17: 873-877, 1999

Sugahara, K. N., T. Teesalu, P. P. Karmali, V. R. Kotamraju, L. Agemy, O. M. Girard, D. Hanahan, R. F. Mattrey, and E. Ruoslahti. Tissue-penetrating delivery of compounds and nanoparticles into tumors. Cancer Cell. 16:510-520, 2009

Templeton, A. C.; Chen, S.; Gross, S. M.; Murray, R. W. Langmuir 1999, 15, 66-76.

Wadia J. S., R. V. Stan, S. F. Dowdy, Transducible TAT-HA fusogenic peptide enhances escape of TAT-fusion proteins after lipid raft macropinocytosis, Nat. Med. 10: 310-315, 2004

Wagner, E. Application of membrane-active peptides for nonviral gene delivery, Adv. Drug Deliv. Rev. 38: 279-289, 1999

Wang G., X. Gao, Y. Huang, Z. Yao, Q. Shi and M. Wu. Nucleophosmin/B23 Inhibits Eg5-mediated Microtubule Depolymerization by Inactivating Its ATPase Activity. The Journal of Biological Chemistry Vol. 285: 19060-19067, 2010.

Zaro J. L., W. C. Shen, Quantitative comparison of membrane transduction and endocytosis of oligopeptides. Biochem. Biophys. Res. C 307: 241-247, 2003

Zhou X Z and K P Lu. The Pin2/TRF1-Interacting Protein PinX1Is a Potent Telomerase Inhibitor. Cell 107, 347-359, 2001.

Ziegler A., P. Nervi, M. Duerrenberger, J. Seelig, The cationic cell-penetrating peptide CPPTAT derived from the HIV-1 protein TAT is rapidly transported into living fibroblasts: optical, biophysical, and metabolic evidence, Biochemistry 44: 138-148, 2005.

The invention claimed is:

1. A method of treating or diagnosing tumors, congenital diseases, nervous system diseases, wound healing, burn repair or inflammatory diseases, said method comprising administering a composition comprising a peptide comprising SEQ ID NO:1 coupled to a substance to be delivered into any required cell compartment to a subject in need thereof, wherein the substance coupled to the peptide comprising SEQ ID NO:1 is selected from the group consisting of: hormonal derivatives, growth factors, proteins, polymers, polysaccharides, enzymes, lipids, nucleic acids, drugs, pharmaceuticals, metals, gold, iron oxide, magnetic compounds, anti-inflammatory agents, analgesic agents, interferons, cytokines, nanoparticles, antibodies, *Salmonella* Flagellin, antitumoral agents, therapeutic agents and diagnostic tracers, wherein the peptide comprising the SEQ ID NO: 1 is selected from the group consisting of: SEQ ID NO: 4, SEQ ID NO: 5, SEQ ID NO: 6, SEQ ID NO: 7, SEQ ID NO: 8, and SEQ ID NO: 9.

2. The method according to claim 1 wherein the peptide comprising SEQ ID NO:1 is linked to a functionalized nanoparticle.

3. The method according to claim 1 wherein the composition further comprises at least one adjuvant.

4. The method according to claim 3, wherein the at least one adjuvant is a polymer.

5. The method according to claim 1, wherein the coupled substance is delivered into the nucleus or nucleolus.

* * * * *

SEQUENCE LISTING

<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Thr Ala Ser Gln Thr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Lys Ser Thr Gln Thr
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic Construct

<400> SEQUENCE: 3

Lys Asn Thr Met Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct

<400> SEQUENCE: 4

Thr Thr Gln Asn Thr Ala Ser Gln Thr
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Thr Val Thr Thr Gln Asn Thr Ala Ser Gln Thr
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

His Pro Ala Glu Pro Gly Ser Thr Val Thr Thr Gln Asn Thr Ala Ser
1               5                   10                  15

Gln Thr Met Ser
            20

<210> SEQ ID NO 7
<211> LENGTH: 45
<212> TYPE: PRT
<213> ORGANISM: Artificial Sequence
<220> FEATURE:
<223> OTHER INFORMATION: Synthetic Construct

<400> SEQUENCE: 7

Met Ser Leu Leu Thr Glu Val Glu Thr Pro Ile Arg Asn Glu Trp Gly
1               5                   10                  15

Ser Arg Ser Asn Gly Ser Ser Asp Pro His Pro Ala Glu Pro Gly Ser
            20                  25                  30

Thr Val Thr Thr Gln Asn Thr Ala Ser Gln Thr Met Ser
        35                  40                  45

<210> SEQ ID NO 8
<211> LENGTH: 12
<212> TYPE: PRT
<213> ORGANISM: Artificial Sequence

```
<220> FEATURE:
<223> OTHER INFORMATION: Synthetic Construct

<400> SEQUENCE: 8

Tyr Thr Thr Gln Asn Thr Ala Ser Gln Thr Met Ser
1               5                   10

<210> SEQ ID NO 9
<211> LENGTH: 20
<212> TYPE: PRT
<213> ORGANISM: Artificial Sequence
<220> FEATURE:
<223> OTHER INFORMATION: Synthetic Construct

<400> SEQUENCE: 9

His Pro Thr Glu Pro Tyr Thr Thr Val Thr Thr Gln Asn Thr Ala Ser
1               5                   10                  15

Gln Thr Met Ser
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic Construct

<400> SEQUENCE: 10

Phe Pro Asn Pro Ser Gly Arg Ser Ser Glu Asp Lys Ser Thr Gln Thr
1               5                   10                  15

Ala Gly

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Pro Lys Asp Asp Lys Asn Thr Met Thr Asp
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Synthetic Construct

<400> SEQUENCE: 12

Ser Leu Val Ser Ser Asp Glu Ser Val Leu His Gly Ser His Glu Ser
1               5                   10                  15

Gly Glu His Val
            20

<210> SEQ ID NO 13
<211> LENGTH: 7345
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(7345)
<223> OTHER INFORMATION: pcAPCH1-Lk1-HA1
```

<400> SEQUENCE: 13

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gcccgacgtc gcatgctccc ggccgccatg gacttcgggt tgagcttggt    960
tttccttgcc cttattttaa aggtgtcca gtgtgacgtg cagctggtgg agtctgggg    1020
agacttagtg cagcctggag ggtccctgaa actctcctgt gcagtctctg gattcacttt   1080
cagtagctat ggcatgtctt gggttcgcca gactccagac aagaggctgg aattggtcgc   1140
aaccattaat gagaatggag gtagcaccta ttatccagac agtgtgaggg gccgtttcac   1200
catctccaga gacaatgccc agaacaccct gtacttgcaa atgagcagtc tgaagtctga   1260
ggatacagcc atgtattact gtgcaaggga gacctccggt agaaggtact ggttttacct   1320
cgatgtctgg ggcgcaggga ccacggtcac cgtctcctca ggaggtggcg gatcaggagg   1380
cggaggttct ggaggaggtg ggagtcaaat tgttctctcc cagtctccag caatcatgtc   1440
tgcatttcca ggggagaggg tcaccatgac ctgcagtgcc agctcaagtg taagttatat   1500
gttctggtac cagcagaagc caggatcctc ccccagactc tgatttatg acacatccaa    1560
cctggcttct ggagtccctg ttcgcttcag tggcagtggg tctgggacct cttactctct   1620
cacaatcagc cgaatggagg ctgaagatgc tgccactttt tactgccaac agtggttttc   1680
ttacccaccg acgttcggtg gaggcaccaa ggtggagatc aaacgggagt tcctaagcc    1740
ctccacccct cctggttctt ccggtggcgc tctcgacgac acaatatgta taggctacca   1800
tgcgaacaat tcaaccgaca ctgttgacac agtactcgag aagaatgtga cagtgacaca   1860
ctctgttaac ctgctcgaag acagccacaa cggaaaacta tgtagattaa aggaatagc    1920
cccactacaa ttggggaaat gtaacatcgc cggatggctc ttgggaaacc cagaatgcga   1980
cccactgctt ccagtgagat catggtccta cattgtagaa acaccaaact ctgagaatgg   2040
aatatgttat ccaggagatt tcatcgacta tgaggagctg agggagcaat tgagctcagt   2100
gtcatcattc gaaagattcg aaatatttcc caaagaaagc tcatggccca accacaacac   2160
aaacggagta acggcagcat gctcccatga ggggaaaagc agttttaca gaaatttgct    2220
atggctgacg gagaaggagg gctcataccc aaagctgaaa aattcttatg tgaacaaaaa   2280
```

```
agggaaagaa gtccttgtac tgtggggtat tcatcacccg cctaacagta aggaacaaca    2340
gaatctctat cagaatgaaa atgcttatgt ctctgtagtg acttcaaatt ataacaggag    2400
atttaccccg gaaatagcag aaagacccaa agtaagagat caagctggga ggatgaacta    2460
ttactggacc ttgctaaaac ccggagacac aataatattt gaggcaaatg gaaatctaat    2520
agcaccaatg tatgctttcg cactgagtag aggctttggg tccggcatca tcacctcaaa    2580
cgcatcaatg catgagtgta acacgaagtg tcaaacaccc ctgggagcta taaacagcag    2640
tctcccttac cagaatatac acccagtcac aataggagag tgcccaaaat acgtcaggag    2700
tgccaaattg aggatggtta caggactaag gaacattccg tccattcaat ccactagtgg    2760
cagcggcagc ggcgaattcc gtttaaacca tcatcatcat catcatcatt aacccgggaa    2820
tcgaattcaa aggcctacgt cgagcggccg ccactgtgct ggatatctgc agaattccac    2880
cacactggac tagtggatcc gagctcggta ccaagcttaa gtttaaaccg ctgatcagcc    2940
tcgactgtgc cttctagttg ccagccatct gttgtttgcc cctcccccgt gccttccttg    3000
accctggaag gtgccactcc cactgtcctt tcctaataaa atgaggaaat tgcatcgcat    3060
tgtctgagta ggtgtcattc tattctgggg ggtggggtgg ggcaggacag caaggggggag    3120
gattgggaag acaatagcag gcatgctggg gatgcggtgg gctctatggc ttctgaggcg    3180
gaaagaacca gctggggctc tagggggtat ccccacgcgc cctgtagcgg cgcattaagc    3240
gcggcgggtg tggtggttac gcgcagcgtg accgctacac ttgccagcgc cctagcgccc    3300
gctcctttcg ctttcttccc ttcctttctc gccacgttcg ccggctttcc ccgtcaagct    3360
ctaaatcggg ggctcccttt agggttccga tttagtgctt tacggcacct cgaccccaaa    3420
aaacttgatt agggtgatgg ttcacgtagt gggccatcgc cctgatagac ggttttttcgc    3480
cctttgacgt tggagtccac gttctttaat agtggactct tgttccaaac tggaacaaca    3540
ctcaacccta tctcggtcta ttcttttgat ttataaggga ttttgccgat ttcggcctat    3600
tggttaaaaa atgagctgat ttaacaaaaa tttaacgcga attaattctg tggaatgtgt    3660
gtcagttagg gtgtggaaag tccccaggct ccccagcagg cagaagtatg caaagcatgc    3720
atctcaatta gtcagcaacc aggtgtggaa agtccccagg ctccccagca ggcagaagta    3780
tgcaaagcat gcatctcaat tagtcagcaa ccatagtccc gcccctaact ccgcccatcc    3840
cgcccctaac tccgcccagt tccgcccatt ctccgcccca tggctgacta attttttta    3900
tttatgcaga ggccgaggcc gcctctgcct ctgagctatt ccagaagtag tgaggaggct    3960
tttttggagg cctaggcttt tgcaaaaagc tcccgggagc ttgtatatcc attttcggat    4020
ctgatcaaga gacaggatga ggatcgtttc gcatgattga acaagatgga ttgcacgcag    4080
gttctccggc cgcttgggtg gagaggctat tcggctatga ctgggcacaa cagacaatcg    4140
gctgctctga tgccgccgtg ttccggctgt cagcgcaggg gcgcccggtt ctttttgtca    4200
agaccgacct gtccggtgcc ctgaatgaac tgcaggacga ggcagcgcgg ctatcgtggc    4260
tggccacgac gggcgttcct tgcgcagctg tgctcgacgt tgtcactgaa gcgggaaggg    4320
actggctgct attgggcgaa gtgccggggc aggatctcct gtcatctcac cttgctcctg    4380
ccgagaaagt atccatcatg gctgatgcaa tgcggcggct gcatacgctt gatccggcta    4440
cctgcccatt cgaccaccaa gcgaaacatc gcatcgagcg agcacgtact cggatggaag    4500
ccggtcttgt cgatcaggat gatctggacg aagagcatca ggggctcgcg ccagccgaac    4560
tgttcgccag gctcaaggcg cgcatgcccg acggcgagga tctcgtcgtg acccatggcg    4620
atgcctgctt gccgaatatc atggtggaaa atggccgctt ttctggattc atcgactgtg    4680
```

```
gccggctggg tgtggcggac cgctatcagg acatagcgtt ggctacccgt gatattgctg    4740
aagagcttgg cggcgaatgg gctgaccgct tcctcgtgct ttacggtatc gccgctcccg    4800
attcgcagcg catcgccttc tatcgccttc ttgacgagtt cttctgagcg ggactctggg    4860
gttcgaaatg accgaccaag cgacgcccaa cctgccatca cgagatttcg attccaccgc    4920
cgccttctat gaaaggttgg gcttcggaat cgttttccgg gacgccggct ggatgatcct    4980
ccagcgcggg gatctcatgc tggagttctt cgcccacccc aacttgttta ttgcagctta    5040
taatggttac aaataaagca atagcatcac aaatttcaca ataaagcat ttttttcact     5100 gcattctagt tgtggtttgt ccaaactcat caatgtatct tatcatgtct gtataccgtc    5160
gacctctagc tagagcttgg cgtaatcatg gtcatagctg tttcctgtgt gaaattgtta    5220
tccgctcaca attccacaca acatacgagc cggaagcata agtgtaaag cctggggtgc     5280 ctaatgagtg agctaactca cattaattgc gttgcgctca ctgcccgctt tccagtcggg    5340
aaacctgtcg tgccagctgc attaatgaat cggccaacgc gcggggagag gcggtttgcg    5400
tattgggcgc tcttccgctt cctcgctcac tgactcgctg cgctcggtcg ttcggctgcg    5460
gcgagcggta tcagctcact caaaggcggt aatacggtta ccacagaat cagggggataa     5520 cgcaggaaag aacatgtgag caaaaggcca gcaaaaggcc aggaaccgta aaaaggccgc    5580
gttgctggcg ttttccata ggctccgccc cctgacgag catcacaaaa atcgacgctc       5640
aagtcagagg tggcgaaacc cgacaggact ataaagatac caggcgtttc ccctggaag     5700 ctccctcgtg cgctctcctg ttccgaccct gccgcttacc ggatacctgt ccgcctttct    5760
cccttcggga agcgtggcgc tttctcatag ctcacgctgt aggtatctca gttcggtgta    5820
ggtcgttcgc tccaagctgg gctgtgtgca cgaaccccc gttcagcccg accgctgcgc      5880
cttatccggt aactatcgtc ttgagtccaa cccggtaaga cacgacttat cgccactggc    5940
agcagccact ggtaacagga ttagcagagc gaggtatgta ggcggtgcta cagagttctt    6000
gaagtggtgg cctaactacg gctacactag aagaacagta tttggtatct gcgctctgct    6060
gaagccagtt accttcggaa aaagagttgg tagctcttga tccggcaaac aaaccaccgc    6120
tggtagcggt ttttttgttt gcaagcagca gattacgcgc agaaaaaaag gatctcaaga    6180
agatcctttg atcttttcta cggggtctga cgctcagtgg aacgaaaact cacgttaagg    6240
gattttggtc atgagattat caaaaaggat cttcacctag atccttttaa attaaaatg     6300 aagttttaaa tcaatctaaa gtatatatga gtaaacttgg tctgacagtt accaatgctt    6360
aatcagtgag gcacctatct cagcgatctg tctatttcgt tcatccatag ttgcctgact    6420
ccccgtcgtg tagataacta cgatacggga gggcttacca tctggcccca gtgctgcaat    6480
gataccgcga acccacgct caccggctcc agatttatca gcaataaacc agccagccgg      6540
aagggccgag cgcagaagtg gtcctgcaac tttatccgcc tccatccagt ctattaattg    6600
ttgccgggaa gctagagtaa gtagttcgcc agttaatagt ttgcgcaacg ttgttgccat    6660
tgctacaggc atcgtggtgt cacgctcgtc gtttggtatg gcttcattca gctccggttc    6720
ccaacgatca aggcgagtta catgatcccc catgttgtgc aaaaaagcgg ttagctcctt    6780
cggtcctccg atcgttgtca gaagtaagtt ggccgcagtg ttatcactca tggttatggc    6840
agcactgcat aattctctta ctgtcatgcc atccgtaaga tgcttttctg tgactggtga    6900
gtactcaacc aagtcattct gagaatagtg tatgcggcga ccgagttgct cttgcccggc    6960
gtcaatacgg gataataccg cgccacatag cagaacttta aaagtgctca tcattggaaa    7020
```

```
acgttcttcg gggcgaaaac tctcaaggat cttaccgctg ttgagatcca gttcgatgta    7080
acccactcgt gcacccaact gatcttcagc atctttact ttcaccagcg tttctgggtg    7140
agcaaaaaca ggaaggcaaa atgccgcaaa aagggaata agggcgacac ggaaatgttg    7200
aatactcata ctcttccttt ttcaatatta ttgaagcatt tatcagggtt attgtctcat    7260
gagcggatac atatttgaat gtatttagaa aaataaacaa atagggggttc cgcgcacatt    7320 tccccgaaaa gtgccacctg acgtc                                          7345
```

<210> SEQ ID NO 14
<211> LENGTH: 6600
<212> TYPE: DNA
<213> ORGANISM: Artificial Sequence
<220> FEATURE:
<223> OTHER INFORMATION: Synthetic Construct
<220> FEATURE:
<221> NAME/KEY: source
<222> LOCATION: (1)..(6600)
<223> OTHER INFORMATION: pcAPCH1-Lk1-4M2

<400> SEQUENCE: 14

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180 ttaggggttag gcgttttgcg ctgcttcgcg atgtacgggc cagatatacg cgttgacatt    240
gattattgac tagttattaa tagtaatcaa ttacgggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaacgg gccgacgtc gcatgctccc ggccgccatg gacttcgggt tgagcttggt    960
tttccttgcc cttatttaa aaggtgtcca gtgtgacgtg cagctggtgg agtctggggg   1020
agacttagtg cagcctggag gtccctgaa actctcctgt gcagtctctg gattcacttt   1080
cagtagctat ggcatgtctt gggttcgcca gactccagac aagaggctgg aattggtcgc   1140
aaccattaat gagaatggag gtagcaccta ttatccagac agtgtgaggg ccgtttcac   1200 catctccaga gacaatgccc agaacaccct gtacttgcaa atgagcagtc tgaagtctga   1260
ggatacagcc atgtattact gtgcaaggga gacctccggt agaaggtact ggttttacct   1320
cgatgtctgg ggcgcaggga ccacggtcac cgtctcctca ggaggtggcg gatcaggagg   1380
cggaggttct ggaggaggtg ggagtcaaat tgttctctcc cagtctccag caatcatgtc   1440
tgcatttcca ggggagaggg tcaccatgac ctgcagtgcc agctcaagtg taagttatat   1500
gttctggtac cagcagaagc caggatcctc ccccagactc ctgatttatg acacatccaa   1560
cctggcttct ggagtccctg ttcgcttcag tggcagtggg tctgggacct cttactctct   1620
```

```
cacaatcagc cgaatggagg ctgaagatgc tgccactttt tactgccaac agtggttttc    1680
ttacccaccg acgttcggtg gaggcaccaa ggtggagatc aaacgggagt ttcctaagcc    1740
ctccacccct cctggttctt ccggtggcgc tctcgagatg agtcttctaa ccgaggtcga    1800 aacgccatc agaaacgaat gggggtctag atctaacggt tcaagtgatc ctatgagtct    1860
tctaaccgag gtcgaaacgc ctatcagaaa cgaatggggg tctagatcta acggttcaag    1920
tgatcctatg agtcttctaa ccgaggtcga aacgccatc agaaacgaat gggggtctag    1980
atctaacggt tcaagtgatc ctatgagtct tctaaccgag gtcgaaacgc ctatcagaaa    2040
cgaatggggg tctagatcta acggttcaag tgatcctact agtcgtttaa accatcatca    2100
tcatcatcat cattaacccg ggaatcgaat tccaccacac tggactagtg gatccgagct    2160
cggtaccaag cttaagttta aaccgctgat cagcctcgac tgtgccttct agttgccagc    2220
catctgttgt ttgcccctcc cccgtgcctt ccttgaccct ggaaggtgcc actcccactg    2280
tcctttccta taaaatgag gaaattgcat cgcattgtct gagtaggtgt cattctattc    2340
tggggggtgg ggtggggcag gacagcaagg gggaggattg ggaagacaat agcaggcatg    2400
ctggggatgc ggtgggctct atggcttctg aggcggaaag aaccagctgg ggctctaggg    2460
ggtatcccca cgcgccctgt agcggcgcat taagcgcggc gggtgtggtg gttacgcgca    2520
gcgtgaccgc tacacttgcc agcgccctag cgcccgctcc tttcgctttc ttcccttcct    2580
ttctcgccac gttcgccggc tttccccgtc aagctctaaa tcggggctc cctttagggt    2640 tccgatttag tgctttacgg cacctcgacc ccaaaaaact tgattaggt gatggttcac    2700 gtagtgggcc atcgccctga tagacggttt ttcgcccttt gacgttggag tccacgttct    2760
ttaatagtgg actcttgttc caaactggaa caacactcaa ccctatctcg gtctattctt    2820
ttgatttata agggattttg ccgatttcgg cctattggtt aaaaaatgag ctgatttaac    2880
aaaaatttaa cgcgaattaa ttctgtggaa tgtgtgtcag ttagggtgtg aaagtcccc    2940 aggctcccca gcaggcagaa gtatgcaaag catgcatctc aattagtcag caaccaggtg    3000
tggaaagtcc ccaggctccc cagcaggcag aagtatgcaa agcatgcatc tcaattagtc    3060
agcaaccata gtcccgcccc taactccgcc catcccgccc ctaactccgc ccagttccgc    3120
ccattctccg ccccatggct gactaatttt ttttatttat gcagaggccg aggccgcctc    3180
tgcctctgag ctattccaga agtagtgagg aggcttttt ggaggcctag gcttttgcaa    3240
aaagctcccg ggagcttgta tatccatttt cggatctgat caagagacag gatgaggatc    3300
gtttcgcatg attgaacaag atggattgca cgcaggttct ccggccgctt gggtggagag    3360
gctattcggc tatgactggg cacaacagac aatcggctgc tctgatgccg ccgtgttccg    3420
gctgtcagcg caggggcgcc cggttctttt tgtcaagacc gacctgtccg gtgccctgaa    3480
tgaactgcag gacgaggcag cgcggctatc gtggctggcc acgacgggcg ttccttgcgc    3540
agctgtgctc gacgttgtca ctgaagcggg aagggactgg ctgctattgg gcgaagtgcc    3600
ggggcaggat ctcctgtcat ctcaccttgc tcctgccgag aaagtatcca tcatggctga    3660
tgcaatgcgg cggctgcata cgcttgatcc ggctacctgc ccattcgacc accaagcgaa    3720
acatcgcatc gagcgagcac gtactcggat ggaagccggt cttgtcgatc aggatgatct    3780
ggacgaagag catcaggggc tcgcgccagc cgaactgttc gccaggctca aggcgcgcat    3840
gcccgacggc gaggatctcg tcgtgaccca tggcgatgcc tgcttgccga atatcatggt    3900
ggaaaatggc cgcttttctg gattcatcga ctgtggccgg ctgggtgtgg cggaccgcta    3960
```

```
tcaggacata gcgttggcta cccgtgatat tgctgaagag cttggcggcg aatgggctga    4020
ccgcttcctc gtgctttacg gtatcgccgc tcccgattcg cagcgcatcg ccttctatcg    4080
ccttcttgac gagttcttct gagcgggact ctggggttcg aaatgaccga ccaagcgacg    4140
cccaacctgc catcacgaga tttcgattcc accgccgcct tctatgaaag gttgggcttc    4200
ggaatcgttt tccgggacgc cggctggatg atcctccagc gcgggatct catgctggag     4260
ttcttcgccc accccaactt gtttattgca gcttataatg gttacaaata aagcaatagc    4320
atcacaaatt tcacaaataa agcatttttt tcactgcatt ctagttgtgg tttgtccaaa    4380
ctcatcaatg tatcttatca tgtctgtata ccgtcgacct ctagctagag cttggcgtaa    4440
tcatggtcat agctgttcc tgtgtgaaat tgttatccgc tcacaattcc acacaacata     4500
cgagccggaa gcataaagtg taaagcctgg ggtgcctaat gagtgagcta actcacatta    4560
attgcgttgc gctcactgcc cgcttccag tcgggaaacc tgtcgtgcca gctgcattaa     4620
tgaatcggcc aacgcgcggg gagaggcggt ttgcgtattg ggcgctcttc cgcttcctcg    4680
ctcactgact cgctgcgctc ggtcgttcgg ctgcggcgag cggtatcagc tcactcaaag    4740
gcggtaatac ggttatccac agaatcaggg gataacgcag gaaagaacat gtgagcaaaa    4800
ggccagcaaa aggccaggaa ccgtaaaaag gccgcgttgc tggcgttttt ccataggctc    4860
cgccccctg acgagcatca caaaaatcga cgctcaagtc agaggtggcg aaacccgaca     4920
ggactataaa gataccaggc gtttccccct ggaagctccc tcgtgcgctc tcctgttccg    4980
accctgccgc ttaccggata cctgtccgcc tttctccctt cgggaagcgt ggcgctttct    5040
catagctcac gctgtaggta tctcagttcg gtgtaggtcg ttcgctccaa gctgggctgt    5100
gtgcacgaac cccccgttca gcccgaccgc tgcgccttat ccggtaacta tcgtcttgag    5160
tccaacccgg taagacacga cttatcgcca ctggcagcag ccactggtaa caggattagc    5220
agagcgaggt atgtaggcgg tgctacagag ttcttgaagt ggtggcctaa ctacggctac    5280
actagaagaa cagtatttgg tatctgcgct ctgctgaagc cagttacctt cggaaaaaga    5340
gttggtagct cttgatccgg caaacaaacc accgctggta gcggtttttt tgtttgcaag    5400
cagcagatta cgcgcagaaa aaaaggatct caagaagatc ctttgatctt ttctacgggg    5460
tctgacgctc agtggaacga aaactcacgt taagggattt tggtcatgag attatcaaaa    5520
aggatcttca cctagatcct tttaaattaa aaatgaagtt ttaaatcaat ctaaagtata    5580
tatgagtaaa cttggtctga cagttaccaa tgcttaatca gtgaggcacc tatctcagcg    5640
atctgtctat ttcgttcatc catagttgcc tgactcccg tcgtgtagat aactacgata     5700
cgggagggct taccatctgg ccccagtgct gcaatgatac cgcgagaccc acgctcaccg    5760
gctccagatt tatcagcaat aaaccagcca gccggaaggg ccgagcgcag aagtggtcct    5820
gcaactttat ccgcctccat ccagtctatt aattgttgcc gggaagctag agtaagtagt    5880
tcgccagtta atagtttgcg caacgttgtt gccattgcta caggcatcgt ggtgtcacgc    5940
tcgtcgtttg gtatggcttc attcagctcc ggttcccaac gatcaaggcg agttacatga    6000
tcccccatgt tgtgcaaaaa agcggttagc tccttcggtc ctccgatcgt tgtcagaagt    6060
aagttggccg cagtgttatc actcatggtt atggcagcac tgcataattc tcttactgtc    6120
atgccatccg taagatgctt ttctgtgact ggtgagtact caaccaagtc attctgagaa    6180
tagtgtatgc ggcgaccgag ttgctcttgc ccggcgtcaa tacgggataa taccgcgcca    6240
catagcagaa ctttaaaagt gctcatcatt ggaaaacgtt cttcggggcg aaaactctca    6300
aggatcttac cgctgttgag atccagttcg atgtaaccca ctcgtgcacc caactgatct    6360
```

```
tcagcatctt ttactttcac cagcgtttct gggtgagcaa aaacaggaag gcaaaatgcc    6420
gcaaaaaagg gaataagggc gacacggaaa tgttgaatac tcatactctt ccttttcaa     6480 tattattgaa gcatttatca gggttattgt ctcatgagcg gatacatatt tgaatgtatt    6540
tagaaaaata aacaaatagg ggttccgcgc acatttcccc gaaaagtgcc acctgacgtc    6600
```